United States Patent
Pourahmadi et al.

(10) Patent No.: US 6,878,540 B2
(45) Date of Patent: *Apr. 12, 2005

(54) DEVICE FOR LYSING CELLS, SPORES, OR MICROORGANISMS

(75) Inventors: Farzad Pourahmadi, Fremont, CA (US); William A. Mcmillan, Cupertino, CA (US); Jesus Ching, Santa Clara, CA (US); Ronald Chang, Redwood City, CA (US); Christel A. Lee, Palo Alto, CA (US); Gregory T.A. Kovacs, Stanford, CA (US); Northrup M. Allen, Berkeley, CA (US); Petersen E. Kurt, San Jose, CA (US)

(73) Assignee: Cepheid, Sunnyvale, CA (US)

( * ) Notice: Subject to any disclaimer, the term of this patent is extended or adjusted under 35 U.S.C. 154(b) by 347 days.

This patent is subject to a terminal disclaimer.

(21) Appl. No.: 10/006,904

(22) Filed: Nov. 7, 2001

(65) Prior Publication Data

US 2002/0045246 A1 Apr. 18, 2002

Related U.S. Application Data

(62) Division of application No. 09/331,911, filed on Jun. 25, 1999, now Pat. No. 6,440,725.

(51) Int. Cl.[7] .............................................. C12M 1/34
(52) U.S. Cl. ............................... 435/287.2; 435/288.5; 435/288.6; 435/306.1; 422/58; 422/68.1; 422/101; 422/104
(58) Field of Search ........................... 435/287.2, 287.3, 435/287.9, 288.5, 288.6, 306.1; 422/58–61, 68.1, 70, 99, 101, 104, 102; 241/2

(56) References Cited

U.S. PATENT DOCUMENTS

| | | | |
|---|---|---|---|
| 3,799,742 A | 3/1974 | Coleman | 23/253 R |
| 4,426,451 A | 1/1984 | Columbus | 436/518 |
| 4,642,220 A | 2/1987 | Björkman | 422/101 |

(Continued)

FOREIGN PATENT DOCUMENTS

| | | |
|---|---|---|
| DE | 19519015 | 9/1996 |
| EP | 0 271 448 | 6/1988 |
| EP | 0 337 690 | 10/1989 |

(Continued)

OTHER PUBLICATIONS

Anderson et al., "Microfluidic Biochemical Analysis System", *Transducers 3 97, Int'l Conf. on Solid0State Sensors and Actuators*, Chicago Jun. 16–19 (1997), p. 477–480.

(Continued)

*Primary Examiner*—David A. Redding
(74) *Attorney, Agent, or Firm*—Townsend and Townsend and Crew LLP

(57) ABSTRACT

A device for use with an ultrasonic transducer to lyse components of a fluid sample comprises a cartridge having a lysing chamber, an inlet port in fluid communication with the lysing chamber, and an outlet port for exit of the sample from the lysing chamber. The inlet and outlet ports are positioned to permit flow of the sample through the lysing chamber, and the chamber contains at least one solid phase for capturing the sample components to be lysed as the sample flows through the chamber. The lysing chamber is defined by at least one wall having an external surface for contacting the transducer to effect the transfer of ultrasonic energy to the chamber.

4 Claims, 16 Drawing Sheets

U.S. PATENT DOCUMENTS

| | | | |
|---|---|---|---|
| 4,789,628 A | 12/1988 | Nayak .......................... 435/7 |
| 4,855,240 A | 8/1989 | Rosenstein et al. ......... 436/514 |
| 4,891,120 A | 1/1990 | Sethi et al. .................. 204/600 |
| 4,895,500 A | 1/1990 | Hok et al. ................... 417/566 |
| 4,908,112 A | 3/1990 | Pace ........................ 204/299 |
| 4,908,318 A | 3/1990 | Lerner ........................ 435/270 |
| 4,915,812 A | 4/1990 | Parce et al. ................. 204/403 |
| 4,918,025 A | 4/1990 | Grenner ...................... 436/165 |
| 4,921,952 A | 5/1990 | Longmire et al. ............ 536/27 |
| 4,923,978 A | 5/1990 | McCormick et al. ......... 536/27 |
| 4,963,498 A | 10/1990 | Hillman et al. ............... 436/69 |
| 4,983,523 A | 1/1991 | Li et al. ..................... 435/173 |
| 5,061,446 A | 10/1991 | Guigan ........................ 422/64 |
| 5,114,858 A | 5/1992 | Williams et al. ............ 435/270 |
| 5,124,444 A | 6/1992 | Van Ness et al. ............. 536/27 |
| 5,155,018 A | 10/1992 | Gillespie et al. ............. 435/91 |
| 5,188,963 A | 2/1993 | Stapleton .................... 435/299 |
| 5,207,988 A | 5/1993 | Lucas .......................... 422/73 |
| 5,223,219 A | 6/1993 | Subramanian et al. ........ 422/55 |
| 5,229,297 A | 7/1993 | Schnipelsky et al. ......... 436/94 |
| 5,234,809 A | 8/1993 | Boom et al. .................. 435/91 |
| 5,296,375 A | 3/1994 | Kricka et al. ............... 435/291 |
| 5,304,487 A | 4/1994 | Wilding et al. ............. 435/291 |
| 5,330,916 A | 7/1994 | Williams et al. ............ 435/311 |
| 5,342,931 A | 8/1994 | Woodard et al. ........... 536/25.4 |
| 5,352,777 A | 10/1994 | Jhingan ..................... 536/25.4 |
| 5,374,353 A | 12/1994 | Murphy ......................... 435/6 |
| 5,374,522 A | 12/1994 | Murphy et al. ................. 435/6 |
| 5,422,241 A | 6/1995 | Goldrick et al. ............... 435/6 |
| 5,427,663 A | 6/1995 | Austin et al. ............ 204/180.1 |
| 5,427,946 A | 6/1995 | Kricka et al. ............... 435/291 |
| 5,438,129 A | 8/1995 | Woodard et al. ........... 536/25.4 |
| 5,443,890 A | 8/1995 | Öhman ....................... 428/167 |
| 5,458,761 A | 10/1995 | Kamahori et al. .......... 204/602 |
| 5,500,071 A | 3/1996 | Kaltenbach et al. .......... 422/70 |
| 5,534,054 A | 7/1996 | Woodard et al. ....... 106/287.11 |
| 5,541,400 A | 7/1996 | Kaltenbach et al. ........ 204/451 |
| 5,543,305 A | 8/1996 | Cummins et al. .......... 435/91.1 |
| 5,580,435 A | 12/1996 | Kovacs ....................... 204/603 |
| 5,580,794 A | 12/1996 | Allen .......................... 436/169 |
| 5,585,069 A | 12/1996 | Zanzucchi et al. .......... 422/100 |
| 5,587,128 A | 12/1996 | Wilding et al. ............... 422/50 |
| 5,605,662 A | 2/1997 | Heller et al. ............... 422/68.1 |
| 5,616,701 A | 4/1997 | Woodard et al. ........... 536/25.4 |
| 5,639,423 A | 6/1997 | Northrup et al. ............. 122/50 |
| 5,639,428 A | 6/1997 | Cottingham ................ 422/112 |
| 5,641,400 A | 6/1997 | Kaltenbach et al. ........ 204/451 |
| 5,652,141 A | 7/1997 | Henco et al. ............... 435/270 |
| 5,693,785 A | 12/1997 | Woodard et al. ........... 536/25.4 |
| 5,705,018 A | 1/1998 | Hartley ....................... 156/345 |
| 5,707,799 A | 1/1998 | Hansmann et al. ............. 435/6 |
| 5,716,852 A | 2/1998 | Yager et al. ................ 436/172 |
| 5,741,639 A | 4/1998 | Ensing et al. ............... 204/452 |
| 5,770,029 A | 6/1998 | Nelson et al. ............... 204/604 |
| 5,777,141 A | 7/1998 | Brunner et al. ............. 554/175 |
| 5,842,787 A | 12/1998 | Kopf-Sill et al. ........... 366/340 |
| 5,843,767 A | 12/1998 | Beattie .................... 435/287.1 |
| 5,846,727 A | 12/1998 | Soper et al. ................. 204/451 |
| 5,856,174 A | 1/1999 | Lipshutz et al. ......... 435/286.5 |
| 5,858,188 A | 1/1999 | Soane et al. ................. 204/450 |
| 5,863,502 A | 1/1999 | Southgate et al. ............ 422/58 |
| 5,863,801 A | 1/1999 | Southgate et al. ............ 436/63 |
| 5,869,004 A | 2/1999 | Parce et al. ................. 422/100 |
| 5,874,046 A | 2/1999 | Megerle .......................... 2/99 |
| 5,880,071 A | 3/1999 | Parce et al. ................. 204/453 |
| 5,921,678 A | 7/1999 | Desai et al. ................. 366/336 |
| 5,928,880 A | 7/1999 | Wilding et al. ............ 435/7.21 |
| 5,972,710 A | 10/1999 | Weigl et al. .................. 436/34 |
| 6,042,709 A | 3/2000 | Parce et al. ................. 204/453 |
| 6,068,752 A | 5/2000 | Dubrow et al. ............. 204/604 |
| 6,080,295 A | 6/2000 | Parce et al. ................. 204/451 |
| 6,090,545 A | 7/2000 | Wohlstadter et al. .......... 435/6 |
| 6,100,084 A | 8/2000 | Miles et al. ............. 435/306.1 |
| 6,153,073 A | 11/2000 | Dubrow et al. ............. 204/453 |
| 6,156,273 A | 12/2000 | Regnier et al. ............... 422/70 |
| 6,168,948 B1 | 1/2001 | Anderson et al. ........ 435/287.2 |
| 6,391,541 B1 * | 5/2002 | Petersen et al. ............... 435/5 |
| 6,431,476 B1 * | 8/2002 | Taylor et al. .................. 241/1 |
| 6,440,725 B1 * | 8/2002 | Pourahmadi et al. .... 435/288.5 |

FOREIGN PATENT DOCUMENTS

| | | |
|---|---|---|
| EP | 0430 248 A2 | 6/1991 |
| EP | 0 576 602 B1 | 11/1995 |
| EP | 0123456 A2 | 1/2000 |
| GB | 938163 | 10/1963 |
| WO | WO 92/05442 | 4/1994 |
| WO | WO 95/12808 | 5/1995 |
| WO | WO 96/07954 | 3/1996 |
| WO | WO 96/12541 | 5/1996 |
| WO | WO 97/02357 | 1/1997 |
| WO | WO 98/08594 | 3/1998 |
| WO | WO 98/10277 | 3/1998 |

OTHER PUBLICATIONS

Brody et al., "Deformation and Flow of Red Cells in a Synthetic Lattice: Evidence for an Active Cytoskeleton", *Biophysical Journal* 68:2224–2232 (1995).

Brody et al., "Diffusion–Based Extraction in a Microfabricated Device", *Sensors and Actuators A* 58:13–18 (1997).

Branebjerg et al., "Fast Mixing by Lamination", Proceedings of the Conference on MEMS, Feb. 11–15, 1996, San Diego, CA.

Buck, George E. et al., *Rapid, Simple Method for Treating Clinical Specimens Containing Mycobacterium tuberculosis To Remove DNA for Polymerase Chain Reaction* Journal of Clinical Microbiology, May 1992, p. 1331–1334.

Cuypers et al., "The NucliSens™ Extractor for Automated Nucleic Acid Isolation", *Infusionsther Transfusionsmed*, 1998;25:117–151.

Klaassen et al., "Silicon Fusion Bonding and Deep Reactive Ion Etching: A New Technology for Microstructures", *Sensors and Actuators A* 52:132–139 (1996).

Maluf, N., "Silicon Fusion Bonding Plus DRIE Delivers Design Flexibility", *Micromachine Devices* 2:4–5 (1997).

B. Sanz et al., *Effect of Ultrasonic Waves on the Heat Resistance Of Bacillus Stearothermophilus Spores* Fundamental And Applied Aspects of Bacterial Spores, 1985, pp. 251–259.

* cited by examiner

US 6,878,540 B2

DEVICE FOR LYSING CELLS, SPORES, OR MICROORGANISMS

CONTINUING APPLICATION DATA

This application is a division of U.S. application Ser. No. 09/331,911, now U.S. Pat. No. 6,440,725, filed Jun. 25, 1999 as a national stage entry (371) of International Application PCT/US98/27632 filed Dec. 24, 1998. All of these applications are incorporated by reference herein for all purposes.

FIELD OF THE INVENTION

This invention relates to a device for lysing cells, spores, or microorganisms.

BACKGROUND OF THE INVENTION

The analysis of clinical or environmental fluids generally involves a series of chemical, optical, electrical, mechanical, or thermal processing steps on the fluid samples. Whether incorporated into a bench-top instrument, a disposable cartridge, or a combination of the two, such processing involves complex fluidic assemblies and processing algorithms.

Contemporary biomedical processing instruments are typically complex, robotically operated devices that move boluses of liquids automatically from one processing region to another. Prior cartridges have also generally processed a fluid sample as a fluid plug or bolus, moving a small quantity of sample from one region to another, where a further process is conducted. For example, Anderson et al. disclose such a device for sample processing in an article entitled "Microfluidic Biochemical Analysis System", Transducers '97, 1997 International Conference on Solid-State Sensors and Actuators, Chicago, Jun. 16–19, 1997, pg. 477–480.

In many analytical procedures, relatively large volumes of liquid (from microliters to milliliters) must be analyzed. Using the bolus approach, such volumes must be held in a container while each operation is performed. While the bolus approach allows for the implementation of complex processing methods, the volume of the fluid sample which can be processed is limited by the size of the individual processing regions, especially where the sample is transiently processed. Thus, the lowest detectable concentration of analyte, i.e. sensitivity, in any assay based on a bolus approach is also limited.

If the container is fabricated with integrated circuit chip technologies (microfluidic chips), the microfabricated chip must be very large to accommodate the relatively large volumes needed to detect a low concentration of analyte. For example, for a 100 microliter volume, a chip at least 1 cm on a side would be required for each bolus processing region. Such a large chip would not only be expensive, but would also defeat the purpose of miniaturization, especially for many types of disposable medical or environmental diagnostic uses.

Present day microfluidic technology has focused on picoliter, nanoliter, and microliter fluid volumes. These small volumes are not practical for many realistic diagnostic applications.

As shown in FIG. 1, the full range of chemical concentrations which one may want to detect in biological samples spans at least 20 orders of magnitude (from 6 copies/mL to $6\times10^{20}$ copies/mL). Therefore, a cartridge for detecting the full range of potential analytes (especially DNA which exists in very low concentration in most biological samples) should be capable of processing large as well as small sample volumes.

Of special interest is the detection of low copy concentrations of analytes such as DNA, in which case large sample volumes are required. For example, the minimum theoretically detectable concentration for DNA probe assays necessitates large sample sizes, such as about $10^{-4}$ liters or more. In detecting infectious diseases, gram negative bacteria can be present at less than 10 copies per milliliter of blood, cryptosporidium generally appears as only a few copies per gallon of drinking water, concentrated biothreat agents, e.g. anthrax, at less than 100 copies per milliliter of water, and food poisoning agents, such as *E. coli* and *salmonella*, may be manifested in less than 10 copies per gram of food.

Thus, sample volumes needed to detect such infectious disease analytes would be larger than those required for detecting analytes present in higher concentrations, as in most clinical and immunochemistry assays. In addition, in the case of more concentrated analytes, such as those in immunoassays and clinical chemistry assays, a large volume sample provides more options for choosing less sensitive detection means, as well as the ability to divide the sample and detect multiple analytes. On the other hand, despite the merits of large sample volumes, it is generally recognized that unique functions can be realized with microfluidic structures, which are generally not compatible with large volumes.

SUMMARY

The processing devices and methodology of the present invention elegantly resolve the dilemma between large sample volumes and microfluidic structures by incorporating microfluidic chips or components into larger cartridges having any desired combination of microscale to macroscale channels, chambers, reservoirs, detection and processing regions. This makes it possible to exploit the key attributes of microfabricated chips and other miniature fluidic or analytical components in a conventional, cartridge-type, physical environment. Such a combination, while superficially less sophisticated than "lab-on-a-chip" technology, affords a superior blend of efficiency and convenience in design, manufacture, and use.

In a preferred embodiment, the invention provides a device for separating a desired analyte from a fluid sample and for concentrating the analyte into a volume of elution fluid smaller than the original sample volume. The desired analyte may comprise, e.g., organisms, cells, proteins, nucleic acid, carbohydrates, virus particles, bacterias, chemicals, or biochemicals. In a preferred use, the desired analyte comprises nucleic acid.

The device comprises a cartridge having formed therein an inlet port for introducing the sample into the cartridge and a sample flow path extending from the inlet port through the body of the cartridge. The sample flow path includes an analyte capture region having at least one flow-through component for capturing the desired analyte from the sample.

The flow-through component is preferably a microfabricated chip having a chamber with internal microstructures formed therein. The microstructures have sufficiently high surface area and binding affinity with the desired analyte to capture the analyte as the sample flows through the chip. The microstructures preferably comprise an array of columns integrally formed with at least one wall of the chamber and extending into the chamber. In an alternative embodiment, the flow-through component comprises a channel or chamber in the cartridge containing at least one solid support for capturing the analyte. Suitable solid supports include, e.g., filters, beads, fibers, membranes, glass wool, filter paper, polymers and gels.

A flow path for carrying elution fluid is also formed in the cartridge. The elution flow path passes through the flow-through component, thereby releasing captured analyte from the component into the elution fluid. The elution flow path diverges from the sample flow path after passing through the component. In the preferred embodiment, the cartridge also includes, or may be coupled to, a heating element for heating the component, thereby increasing elution efficiency.

The cartridge also includes at least one flow controller, e.g., one or more valves, flow diverters, or fluid diodes, for directing the fluid sample into the sample flow path after the sample flows through the capture component and for directing the elution fluid and eluted analyte into the elution flow path after the elution fluid flows through the capture component. In the preferred embodiment, the cartridge further includes a waste chamber at the end of the sample flow path for collecting the remaining fluid sample and a second chamber at the end of the elution flow path for receiving the eluted analyte. The second chamber may alternatively be a reaction chamber formed in a separate reaction vessel coupled to the cartridge to receive the eluted analyte for further processing.

In contrast to prior fluidic cartridges that process a fluid sample as a bolus, the continuous-flow cartridge of the present invention permits the rapid processing of a fluid sample that is larger in volume than any interactive region within the cartridge. The ability to process larger sample volumes allows increased sensitivity in the detection of low copy concentrations of analytes, such as nucleic acid.

In a preferred mode of operation, the cartridge is used to separate nucleic acid, e.g. DNA or RNA, from a fluid sample and to concentrate the nucleic acid into a smaller volume of elution fluid. In these applications, it is preferred that the sample flow path formed in the cartridge include a lysing region, e.g. a channel or chamber, for lysing cells, spores, or microorganisms in the fluid sample. Preferably, an ultrasonic transducer, such as an ultrasonic horn, is coupled to the cartridge for transferring ultrasonic energy to the fluid sample in the lysing region, thereby effecting lysis of the cells, spores, or microorganisms. The lysing channel or chamber may additionally include particles or beads for rupturing the cells, spores, or microorganisms as the ultrasonic energy is applied.

The lysing channel or chamber preferably contains a solid phase for capturing the cells, spores, or microorganisms as the sample flows through the chamber. Suitable solid phases include, e.g., filters, beads, fibers, membranes, glass wool, filter paper, polymers and gels. Lysing is accomplished by applying ultrasonic energy to the cells, spores, or microorganisms captured on the solid phase. The ultrasonic energy may be supplied from, e.g., an ultrasonic horn coupled to a wall of the lysing chamber or built into the cartridge. The cartridge may also contain, or be coupled to, a heating element in thermal contact with the lysing chamber for heating the fluid sample as the ultrasonic energy is applied.

In another embodiment of the cartridge, the lysing region comprises a lysing chamber positioned upstream of the capture region, and the cartridge further includes a reagent chamber in fluid communication with the lysing chamber for holding a lysing reagent. In this embodiment, a fluid motive source, such as a pump, is also provided for forcing the lysing reagent to flow into the lysing chamber to contact the sample. Lysing reagents may also be used in combination with the ultrasonic lysing embodiments described above.

In the preferred embodiment, the invention also provides an external instrument for receiving one or more of the cartridges. The external instrument includes a fluid motive source, e.g., one or more pumps, vacuums, or pressure sources, that interface with one or more ports or vents formed in the cartridge, to force the sample to flow through the cartridge. Either the instrument or the cartridge may also include processing electronics, e.g., one or more microprocessors, microcontrollers, or memory chips, for controlling the operation of the cartridge.

DETAILED DESCRIPTION

Figure 1:
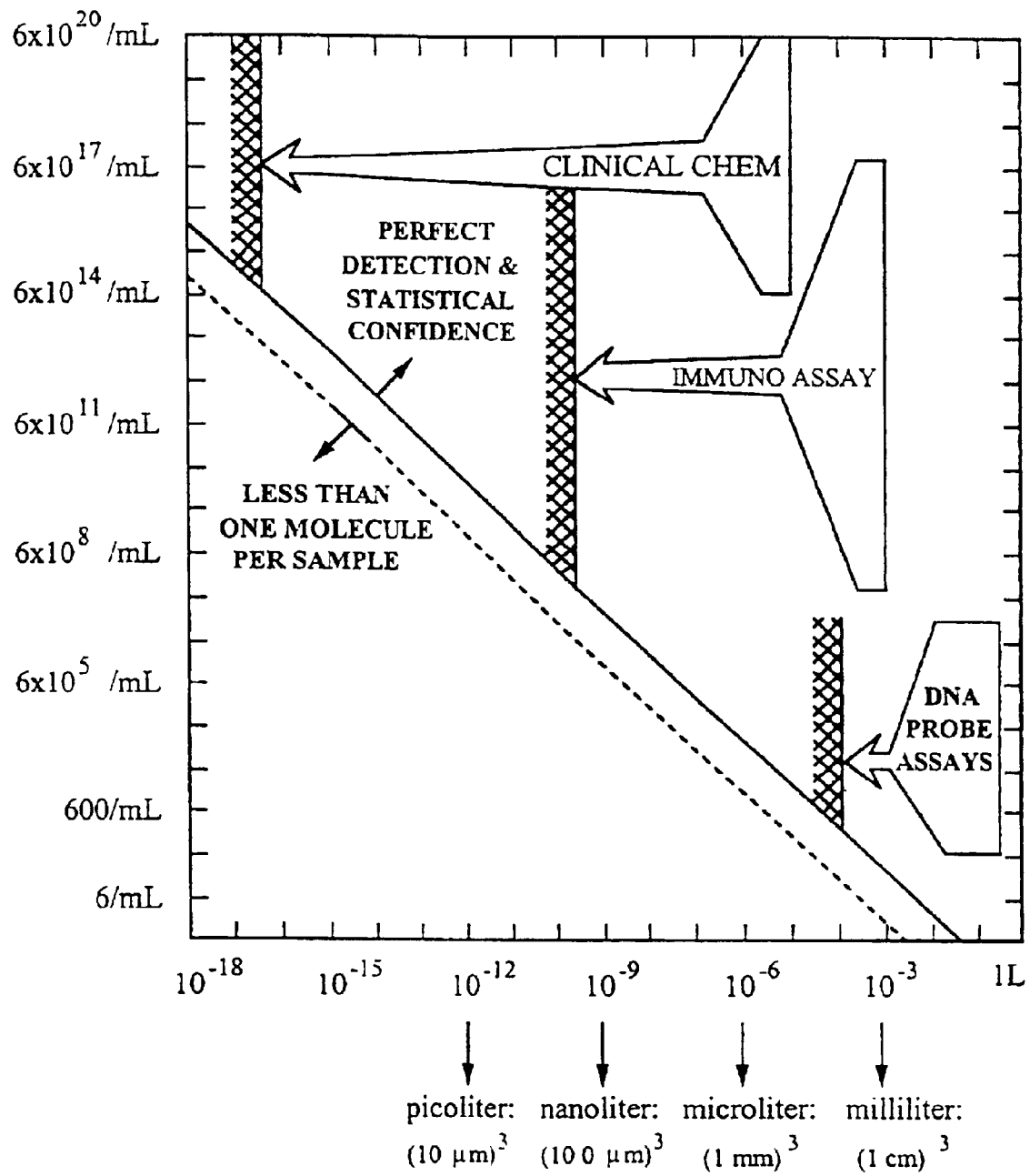
FIG. 1 is a plot of analyte concentration (copy number) versus sample volume showing the minimum volume required for statistically significant detection of analyte.

The present invention provides a cartridge for performing various operations on a fluid sample as the sample flows through a series of interconnected, interactive regions within the cartridge. The regions are located sequentially along a fluid flow path through the cartridge, so that a segment of the fluid stream is exposed to a specific operation at one region, then another operation at the next region, etc. The sample flows through the interactive regions so that it is simultaneously in contact with more than one region at a given time. The sample flow is preferably continuous, so that the operations at each region occur simultaneously and sequentially on the fluid stream.

The cartridges of the present invention allow for significantly improved processing of a fluid sample for the detection and/or analysis of chemical components in the sample, such as biological molecules. A pioneering improvement over the prior art is the ability to rapidly process a fluid sample that is larger in volume than any interactive region within the cartridge, thereby permitting increased sensitivity in the detection of low copy concentrations of analytes, such as nucleic acid. The cartridges may also be designed to automatically conduct processes, such as mixing reagents with the fluid sample, lysing, filtering, and introducing the mixture into a reaction chamber or separate reaction vessel appropriate for further processing, e.g., detection or amplification of the analyte.

Since the operations on the fluid sample are performed on the sample stream as it flows through the various regions of the cartridge, any incorporated microfluidic processing chip or other component can be very small, as much as one hundred times smaller than with the bolus-oriented approach. This allows the entire processing facility to be small, yet capable of processing relatively large fluid samples (e.g., 0.1 to 10 mL), and thus to take advantage of the unique properties of very small microfluidic chips or other fluid processing components.

In a preferred embodiment, the invention provides a device for separating a desired analyte from a fluid sample and for concentrating the analyte into a volume of elution fluid smaller than the original sample volume. The desired analyte may comprise, e.g., organisms, cells, proteins, nucleic acid, carbohydrates, virus particles, bacterias, chemicals, or biochemicals. In a preferred use, the desired analyte comprises nucleic acid.

As used herein, the term "nucleic acid" refers to any synthetic or naturally occurring nucleic acid, such as DNA or RNA, in any possible configuration, i.e., in the form of double-stranded nucleic acid, single-stranded nucleic acid, or any combination thereof. As used herein, the term "fluid sample" includes both gases and liquids, preferably the latter. The fluid sample may be an aqueous solution containing particles, cells, microorganisms, ions, or small and large molecules, such as proteins and nucleic acids, etc. In a particular use, the fluid sample may be a bodily fluid, e.g., blood or urine, or a suspension, such as pulverized food. The fluid sample may be pretreated, for example, mixed with chemicals, centrifuged, pelleted, etc., or the fluid sample may be in a raw form.

Figure 2:
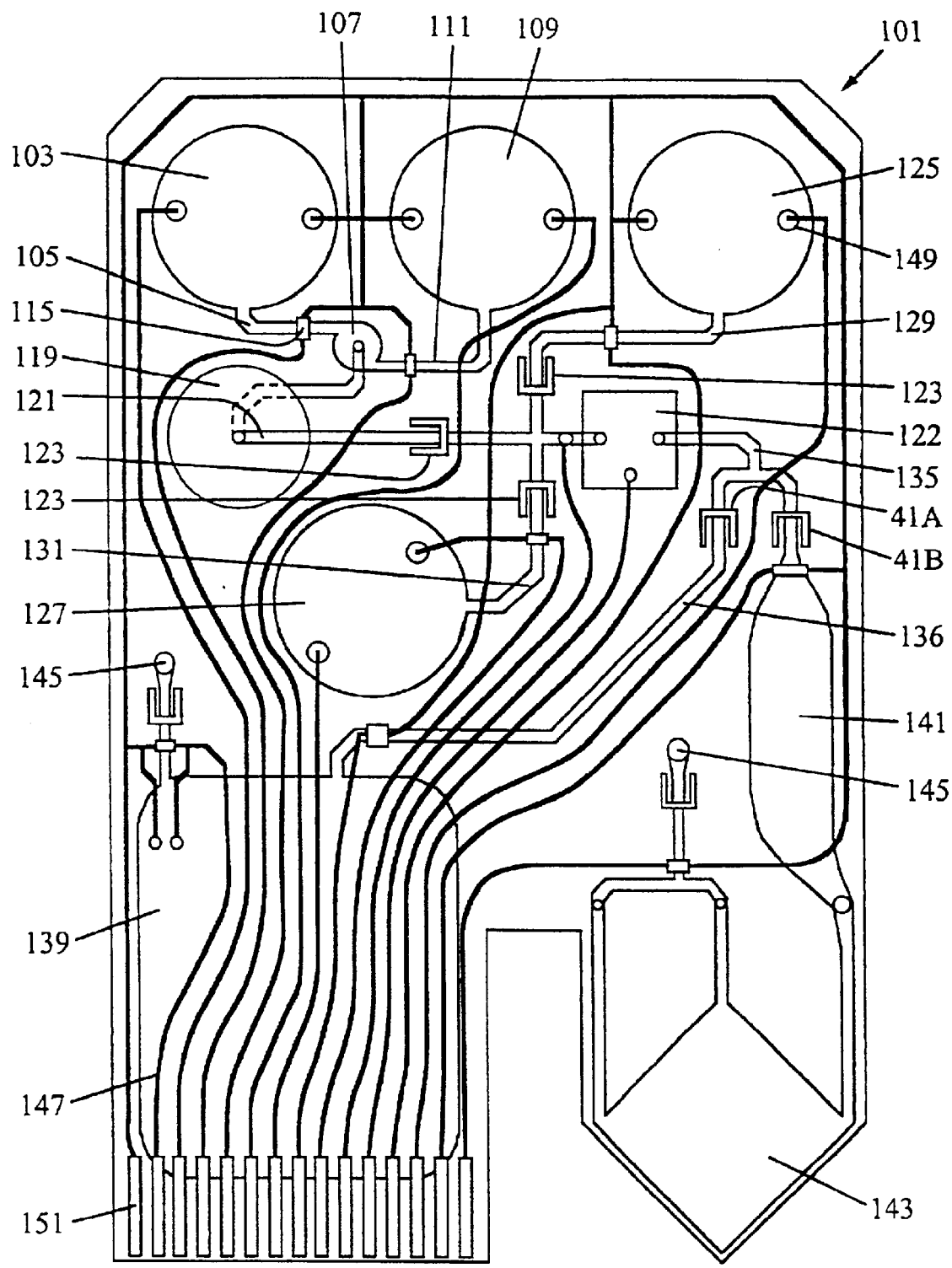
FIG. 2 is a schematic, plan view of a cartridge for processing a fluid sample according to a first embodiment of the invention.

FIG. 2 shows an example of a cartridge 101 according to a preferred embodiment of the invention. The cartridge is designed to process a fluid sample and amplify nucleic acids, such as by polymerase chain reaction (PCR). The cartridge 101 includes a sample port 103 for introducing a fluid sample into the cartridge and a sample flow path extending from the port 103 into the body of the cartridge.

The sample flow path includes a channel 105 leading from the sample port 103 to a mixing chamber 107 for mixing of the sample with lysing reagents. The sample flow path also includes a lysing chamber 119 where the sample contacts a filter to capture components, e.g., cells, spores, or microorganisms in the sample. The captured components are lysed in chamber 119. The sample flow path further includes a flow-through component 122 for capturing a desired analyte, e.g. nucleic acid, from the sample as the sample flows through the component 122.

The flow-through component 122 is preferably a microfabricated chip having a chamber with internal microstructures formed therein. The microstructures have sufficiently high surface area and binding affinity with the desired analyte to capture the analyte as the sample flows through the chip. The microstructures preferably comprise an array of columns integrally formed with at least one wall of the chamber and extending into the chamber. Various embodiments of the microfabricated chip are described in detail below with reference to FIGS. 6–14.

In an alternative embodiment, the flow-through component 122 comprises a channel or chamber formed in the cartridge. The channel or chamber contains at least one solid support for capturing the desired analyte from the fluid sample as the sample flows through the solid support. Suitable solid supports include filters, beads, fibers, membranes, glass wool, filter paper, polymers and gels.

The sample flow path also includes a channel 135 leading to flow controllers 41A and 41B, and a channel 136 leading to a vented waste chamber 139. The flow controllers 41A and 41B are arranged to direct the sample into the waste chamber 139 after the sample flows through the capture component 122. The flow controllers 41A and 41B may be, e.g., valves, flow diverters, or fluid diodes.

A flow path for carrying elution fluid is also formed in the cartridge 101. In the preferred embodiment, the cartridge includes a storage chamber 127 for storing elution fluid. The elution flow path extends from the chamber 127 through a channel 131 and passes through the flow-through component 122, thereby releasing captured analyte from the component into the elution fluid. In an alternative embodiment, the cartridge includes a separate inlet port, in place of or in addition to the storage chamber 127, for introducing elution fluid into the cartridge from an external source.

The elution flow path diverges from the sample flow path after passing through the component 122. In this example, the elution flow path follows the channel 135 to the flow controllers 41A and 41B. The flow controllers 41A and 41B are arranged to direct the elution fluid and eluted analyte into a reagent chamber 141 containing PCR reagents. The reagent chamber 141 is in fluid communication with a reaction chamber 143 for PCR amplification.

The reaction chamber 143 may be a chamber formed in the cartridge 101. Alternatively, the reaction chamber 143 may be formed in a separate reaction vessel designed to be coupled to the cartridge to receive the eluted analyte. Suitable reaction vessels for this purpose are disclosed in International Application Number PCT/US98/03962 filed Mar. 2, 1998 and entitled "Heat Exchanging, Optically Interrogated Chemical Reaction Assembly", the disclosure of which is incorporated by reference herein. The application also teaches a thermal sleeve for receiving and thermally cycling the reaction chamber. For this reason, it is advantageous for the reaction chamber to protrude from the rest of the cartridge body to facilitate insertion of the reaction chamber into the thermal sleeve.

The cartridge 101 also includes a storage chamber 109 for storing a lysing reagent, and a storage chamber 125 for storing a washing reagent. The cartridge 101 further includes flow controllers 123, such as valves or fluid diodes, for controlling the flow of fluid through the cartridge. The cartridge 101 also preferably includes resistive sensors 115 for sensing the presence of fluid in various channels and regions.

Figure 3:
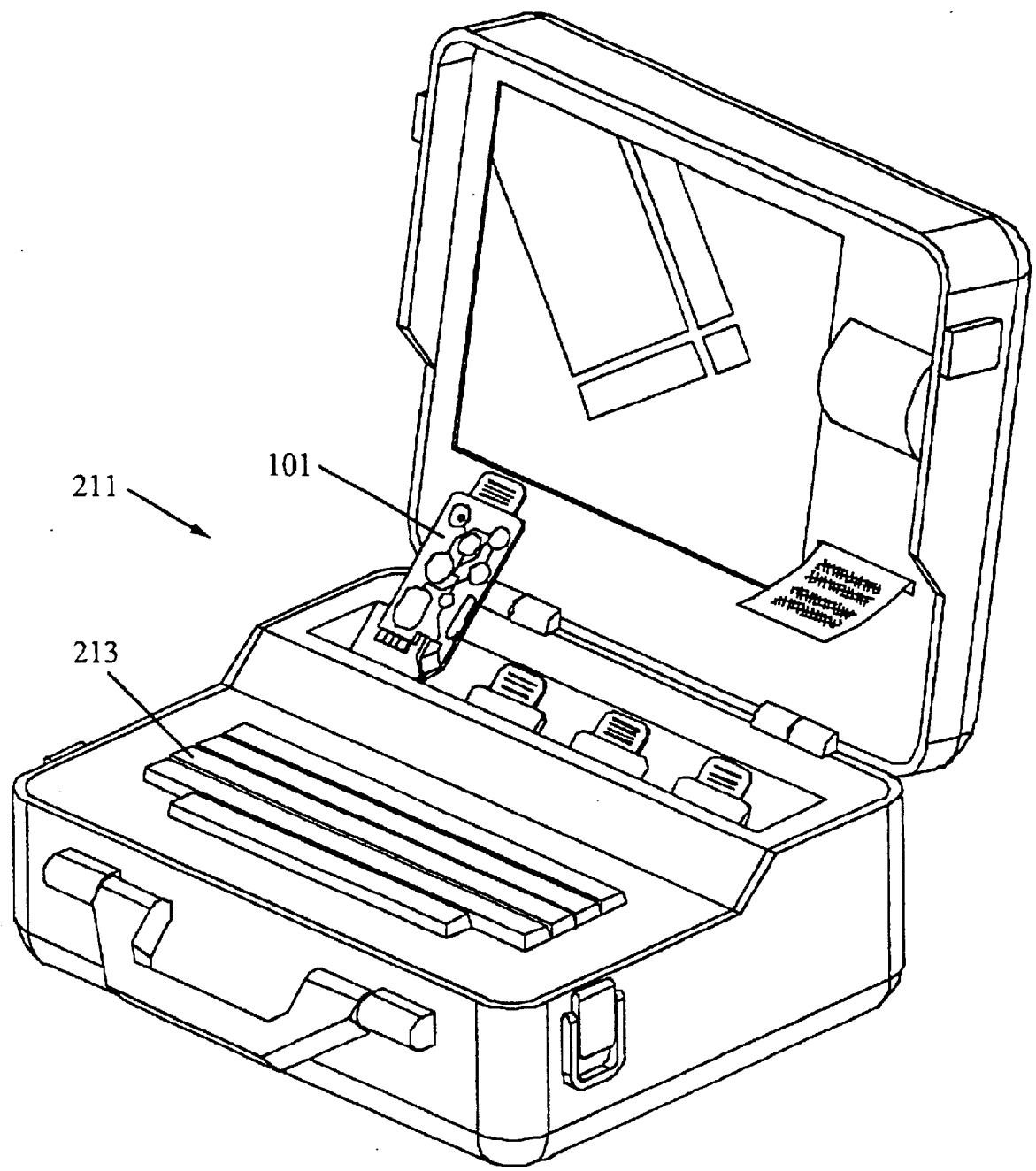
FIG. 3 is a perspective view of an instrument holding several cartridges for processing.

Referring to FIG. 3, the cartridge 101 is preferably used in combination with a portable, i.e. hand-held or desk-top, external instrument 211 designed to accept one or more of the cartridges 101. The connection between the disposable cartridge 101 and the external instrument 211 is preferably by means of a thin, card-like section of the cartridge 101, and a mating connector within the instrument 211. This type of connection is similar to the standard card edge connectors used with printed circuit boards in, e.g., personal computers or card cages.

As shown in FIG. 2, narrow fingers 151 of conductive material on the card or on foil come in contact with gold connectors in the instrument as the cartridge 101 is inserted for processing. Many connections can be made within a small width of cartridge in this implementation. In the case of the cartridge, the card may be a thin section of molded plastic or a sheet on which conductive materials are deposited.

Electrical connections may also be used to transfer information to and from stored memory and/or intelligence on the cartridge 101. For example, a memory or microprocessor chip may be incorporated as part of the cartridge. This chip preferably contains information such as the type of cartridge, program information such as specific protocols for the processing of the cartridge, tolerances for accept and reject, serial numbers and lot codes for quality tracking, and provision for storing the results of the processing.

Integrated electronic memory on the cartridge 101 allows for rapid, easy, and error-free set-up of the instrument 211 for different fluidic processing protocols. When a cartridge is inserted into the instrument, the instrument may electronically address the memory on the cartridge, and thus automatically receive the appropriate set of instructions for controlling the time-sequence of fluidic operations to be carried out with the inserted cartridge. The instrument 211 may simply sequentially retrieve and execute each step in the cartridge's memory, or download its contents so that the user may edit the sequence using, e.g., keyboard 213.

If suitable memory is included on the cartridge, such as writable memory (e.g., erasable programmable read-only memory (EPROM), electrically erasable programmable read-only memory (EEPROM), etc., intermediate and final results, based on the sample introduced into the cartridge, could be written by the instrument into the cartridge's memory for co-located storage with the physical sample after processing. This is particularly advantageous in applications where archiving of samples and results is necessary, such as forensics.

In addition, other information can be stored in the memory on the cartridge, in unalterable (or alterable) forms. For example, cartridge serial number, lot manufacture information, and related information could be pre-programmed and unalterable. User data, technician identification number, date of test, location of test and instrument serial number could be unalterably written into the cartridge. This allows for easy identification of the "chain of custody" in the handling of a specimen. Engineers skilled in the art of data storage will recognize that other memory means than electronic can be used, such as optically-addressed printed regions (e.g., ink-jet or thermal), magnetic strips, etc.

Electrical power may be provided to the cartridge 101 from the external instrument 211. Alternatively, instead of making the instrument bulkier and heavier by adding batteries to accommodate the power needs of multiple cartridges used sequentially to process many samples, the power source for each cartridge may be included on the cartridge, sufficient to power the instrument and cartridge.

The instrument 211 preferably includes processing electronics, e.g., one or more microprocessors, multiplexers, power control circuits, and sensor circuits, for controlling the operation of the cartridge 101. The processing electronics are connected by the contact fingers 151 and electrical leads 147 to various regions, storage areas, pumps, sensors, and channels in the cartridge 101. Alternatively, there may be other data links of the cartridge to the instrument, such as radio frequency or infrared links. Although the processing electronics are physically located in the external instrument 211 in the preferred embodiment, it is to be understood that the processing electronic may also be located on the cartridge 101.

Both external and internal fluid motive sources are suitable for use with the cartridges disclosed herein. The fluid motive source may be contained in or on the cartridge 101 itself, or may be external to the cartridge, e.g., included in the external instrument 211 into which the cartridge 101 is inserted for processing. One type of fluid motive source described in this disclosure is an electrolytic pump (e-pump) located inside the cartridge 101. The fluid inside a sealed pouch is decomposed into gaseous elements by an electrical current, thereby pressurizing and expanding the pouch. This sealed pumping pouch, or e-pump, is positioned against a reagent pouch and forces the contents of the reagent pouch into the fluidic circuit as the pumping pouch expands.

Other types of fluid motive sources may also be used with the cartridges of the present invention. For example, a stepper motor or solenoid can be used to provide a force and press against a reagent pouch inside the cartridge, thereby forcing the contents of the reagent pouch into the fluidic circuit. Alternatively, a mechanical spring located either inside the cartridge or inside the external instrument may provide the motive source for pressing on the reagent pouch and forcing the reagent into the fluidic circuit. The mechanical energy stored in the spring may either be built into the cartridge during manufacture or be generated during insertion of the cartridge into the instrument (i.e. cocking the spring during manual insertion of the cartridge).

Other potential fluid motive sources include a pneumatic pressure source (or vacuum source) located inside the cartridge or inside the instrument. Such a fluid motive source may be provided by a pressurized (or evacuated) canister, chip, or other container. The motive source could also be a compressor or vacuum pump located either inside the cartridge or inside the instrument. In the instances in which an external pressure or vacuum motive source is used, the cartridge has suitable ports, vents, or channels for interfacing with the source. Likewise, electrophoretic or electroosmotic sources may be employed. Piezoelectrically, magnetically, or electrostatically driven membrane pumps or valves could also be incorporated into the cartridge or permanently installed in the instrument so that the devices are mechanically interfaced with the cartridge when the cartridge is inserted into the instrument.

In operation, a fluid sample containing a desired analyte. e.g. nucleic acid, is added to the sample port 103 of the cartridge 101 and forced to flow continuously (such as with an electrolytic or mechanical pump) down a channel 105 and into the mixing chamber 107. Lysing reagents are simultaneously released from the storage chamber 109 and forced to flow down a channel 111 and into the chamber 107. Suitable lysing reagents include, for example, solutions containing a chaotropic salt, such as guanidine HCl, guanidine thiocyanate, guanidine isothiocyanate, sodium iodide, urea, sodium perchlorate, and potassium bromide.

The fluid sample and lysing reagents traveling in the channels 105 and 111, respectively, are detected by resistive sensors 115. As the lysing reagent contacts the fluid sample, cells, spores, or microorganisms present in the fluid sample begin to be lysed. The fluid sample and lysing reagent continue to flow into the lysing chamber 119 where the sample contacts a filter and the cells, spores, or microorganisms are captured. The lysing reagent continues to lyse the captured sample components. The filter also serves to remove debris from the fluid sample. In another important embodiment of the invention, an ultrasonic transducer is coupled to the cartridge 101 next to lysing chamber 119, e.g. coupled to a wall of the chamber 119, and the sample components are lysed by ultrasonic energy provided by the transducer. Various ultrasonic lysing embodiments are discussed in greater detail below with reference to FIGS. 19–20.

The lysed sample proceeds from the lysing chamber 119 down channel 121 and is forced to flow through the capture component 122. As the fluid sample and lysing reagent flow through the component 122, nucleic acid in the fluid sample binds to the component 122. The flow rate of the fluid sample through the component 122 is preferably in the range of 0.1 to 50 µL/sec. The fluid sample and lysing reagent exiting the component 122 flow down channel 135, through the flow controller 41A, and through channel 136 to the waste chamber 139. In another embodiment, after flowing through the component 122, the fluid sample may be redirected to recirculate through the component additional times.

After the fluid sample is forced to flow through the component 122, the washing reagent in storage region 125 is forced to flow down a channel 129 and through the component 122. The wash flow rate is preferably on the range of 0.5 to 50 µL/sec. Fluid is prevented from flowing upstream in the cartridge by flow controllers 123 in channels 121, 129, and 131. The washing reagent washes residual contaminants, such as chaotropic salts, from the component 122. A variety of suitable wash solutions of varying pH, solvent composition, and ionic strength may be used for this purpose and are well known in the art. For example, a suitable washing reagent is a solution of 80 mM potassium acetate, 8.3 mM Tris-HCl, pH 7.5, 40 uM EDTA, and 55% ethanol. The washing reagent continues to flow through the flow controller 41A and into the waste chamber 139.

After washing the component 122, elution fluid from the storage region 127 is forced to flow down channel 131 and through the component 122, thus releasing the nucleic acid from the component into the elution fluid. At this point, the flow controllers 41A and 41B are reconfigured to prevent the elution fluid from flowing through the flow controller 41A and to permit the elution fluid to flow through the flow controller 41B into the reagent chamber 141. The flow rate of elution fluid through the component 122 is preferably in the range of 0.1 to 10 µL/sec. The flow rate of the elution fluid may be relatively slow as compared to the flow rate of the fluid sample to allow for more analyte to be released from the component.

In general, any suitable elution fluid may be used to elute nucleic acid from the component 122. Such elution fluids are well known in the art. For example, the elution fluid may comprise molecular grade pure water, or alternatively, a buffer solution, including but not limited to a solution of TRIS/EDTA; TRIS/acetate/EDTA, for example 4 mM Tris-acetate (pH 7.8), 0.1 mM EDTA, and 50 mM NaCl; TRIS/borate; TRIS/borate/EDTA; potassium phosphate/DMSO/glycerol; NaCl/TRIS/EDTA; NaCl/TRIS/EDTA/TWEEN; TRIS/NaCl/TWEEN; phosphate buffers; TRIS buffers; HEPES buffers; nucleic acid amplification buffers; nucleic acid hybridization buffers, etc.

Prior to forcing the elution fluid to flow through the component 122, an intermediate air-gap step may optionally be performed. A gas, preferably air, may be forced to flow through component 122 after the wash solution flows through and before the elution fluid flows through. The air-gap step provides for clear separation of liquid phases, and helps at least substantially dry the component 122 of any remaining wash solution prior to elution.

The component 122 is preferably heated as the elution fluid is forced to flow through it to increase elution efficiency. The heating is preferably performed by supplying power to a resistive heating element in a closed loop feedback system under the control of the processing electronics in the cartridge. In the preferred embodiment, the component 122 is heated to a temperature in the range of 60 to 95° C. as the elution fluid flows through the it.

Elution fluid containing the nucleic acid exits the component 122 and travels down the channel 135 to the reagent chamber 141. The elution fluid and nucleic acid contact and reconstitute dried PCR reagents contained in the chamber 141, and the elution fluid, nucleic acid, and PCR reagents continue to flow into reaction chamber 143 for PCR amplification and detection. In an alternative embodiment, the elution solution already includes PCR reagents so that the reagent need not be dried in the chamber 141. Vents 145 in communication with the waste chamber 139 and the reaction chamber 143 allow release of gases during the process.

One advantage of the continuous-flow cartridge of the preferred embodiment is that it allows the analyte, e.g. nucleic acid, from a relatively large volume of fluid sample, e.g. several milliliters or more, to be concentrated into a much smaller volume of elution fluid, e.g., 25 µL or less. In contrast to prior art devices, the cartridge of the present invention permits extraordinary concentration factors by efficiently extracting analyte from milliliter quantities of fluid sample and eluting the analyte into microliter quantity eluates. In the preferred embodiment, the sample volume forced to flow through the cartridge is in the range of 1 to 100 mL, enabling concentration factors of 100 or greater. For example, the analyte from 1 mL of fluid sample may be captured in the device and concentrated into 10 µL or less of elution fluid.

A fluid sample may be introduced into the cartridge by a variety of means, manual or automated. For manual addition, a measured volume of material may be placed into a receiving area of the cartridge through an input port and a cap is then placed over the port. Alternatively, a greater amount of sample material than required for the analysis can be added to the cartridge and mechanisms within the cartridge can effect the precise measuring and aliquoting of the sample needed for the specified protocol.

It may be desirable to place certain samples, such as tissue biopsy material, soil, feces, exudates, and other complex material into another device or accessory and then place the secondary device or accessory into the cartridge causing a mechanical action which effects a function such as mixing, dividing, or extraction. For example, a piece of tissue may be placed into the lumen of a secondary device that serves as the input port cap. When the cap is pressed into the port, the tissue is forced through a mesh that slices or otherwise divides the tissue.

For automated sample introduction, additional cartridge design features are employed and, in many cases, impart specimen accession functionality directly into the cartridge. With certain samples, such as those presenting a risk of hazard to the operator or the environment, such as human retrovirus pathogens, the transfer of the sample to the cartridge may pose a risk. Thus, in one embodiment, a syringe may be integrated into a device to provide a means for moving external fluidic samples directly into the cartridge. Alternatively, a venous puncture needle and an evacuated blood tube can be attached to the cartridge forming an assembly that can be used to acquire a sample of blood. After collection, the tube and needle are removed and discarded, and the cartridge is then placed in an instrument to effect processing. The advantage of such an approach is that the operator or the environment is not exposed to pathogens.

The input port can be designed with a consideration of appropriate human factors as a function of the nature of the intended specimen. For example, respiratory specimens may be acquired from the lower respiratory tract as expectorants from coughing, or as swab or brush samples from the back of the throat or the nares. In the former case, the input port can be designed to allow the patient to cough directly into the cartridge or to otherwise facilitate spitting of the expectorated sample into the cartridge. For brush or swab specimens, the specimen is placed into the input port where features of the port and closure facilitate the breaking off and retaining of the end of the swab or brush in the cartridge receiving area.

In another embodiment, the cartridge includes input and output tubes that may be positioned in a sample pool of very large volume, such as a flowing stream of water, so that the sample material flows through the cartridge. Alternatively, a hydrophilic wicking material can serve as an interactive region so that the entire cartridge can be immersed directly into the specimen, and a sufficient amount of specimen is absorbed into the wicking material. The cartridge is then removed, and can be transported to the laboratory or analyzed directly using a portable instrument. In another embodiment, tubing can be utilized so that one end of the tube is in direct communication with the cartridge to provide a fluidic interface with at least one interactive region and the other end is accessible to the external environment to serve as a receiver for sample. The tube can then be placed into a specimen and serve as a sipper.

The cartridge itself may also serve as the actual specimen collection device, thereby reducing handling and inconvenience. In the case of specimens involved in legal disputes or criminal investigations, the direct accessing of the test material into the fluidic cartridge is advantageous because the chain of custody is conveniently and reliably preserved.

In general applications of the cartridge, chemical interactions of the fluid sample with one or more reagents may be required, so it is desirable to include interactive regions that provide for chemical reagents, the number and type depending on the specific analytical protocol to be facilitated. Multiple interactive regions, each containing different reagents, can be arranged in series to enable the sequential processing of the sample.

Reagents may be exogenously introduced into the cartridge before use, e.g., through sealable openings in each region of the cartridge. Alternatively, the reagents may be placed in the cartridge during manufacture. The reagents may be disposed within the interactive regions that perform the operations for which the reagents will be used, or within regions leading to a particular interactive region. Alternatively, the reagents may be disposed within storage chambers in fluid communication with interactive regions.

The type of reagent utilized at an interactive region depends, inter alia, on the fluid characteristics and size of the sample, the nature and concentration of the target constituents, and the desired processing protocol. In the case of solution phase interactions, the reagents may be aqueous solutions or dried reagents requiring reconstitution. The particular format is selected based on a variety of parameters, including whether the interaction is solution-phase or solid-phase, the inherent thermal stability of the reagent, speed of reconstitution, and reaction kinetics.

Liquid reagents may include, but are not limited to, buffer solutions such as saline, TRIS, acids, bases, detergent solutions, and chaotropic solutions, which are commonly used for DNA and RNA purification and washing. Dried reagents can be employed as precursor materials for reconstitution and solution-phase interaction or as solid-phase reagents, including pH indicators; redox indicators; enzymes such as horseradish peroxidase, alkaline phosphatase, reverse transcriptase, DNA polymerase, and restriction enzymes; enzyme substrates; enzyme-antibody or enzyme-antigen conjugates; DNA primers and probes; buffer salts; and detergents. Furthermore, solid-phase reagent coatings such as serum albumin, streptavidin, and a variety of cross-linkable proteins such as polysaccharides may be employed at the interactive region.

Dried reagents may also be contained within a membrane material that can be employed as an interactive region by physical incorporation of the material into a region in communication with fluidic channels. Cellulose, nitrocellulose, polycarbonate, nylon, and other materials commonly used as membrane materials can be made to contain reagents. Such membranes are designed to capture target cells, effect lysis of host cells, release target nucleic acids, and separate contaminants that may interfere with the polymerase chain reaction or other analytical events. These papers may be positioned within a region to enable cross-flow or tangential flow of fluids. Because the papers can simultaneously physically entrap target cells, lyse cells, and bind either target analytes or competing contaminants or analytical reaction inhibitors, they provide for multiple modes of activity at a single interactive region within the cartridge.

Reagents can be contained as liquids within specific regions of the cartridge, using conventional pouching or packaging techniques, the designs of which are optimized to allow integration into the cartridge. Reagents containing compounds that are thermally unstable when in solution can be stabilized by drying using common techniques such as lyophilization. Additives, such as simple alcohol sugars, methylcelluloses, and bulking proteins may be added to the reagent before drying to increase stability or reconstitutability. For these reagents, reagent activity is reconstituted by rehydration with the fluid sample or with a separate reconstitution fluid, either by pre-mixing or preferably during sample flow.

A variety of techniques may be employed which provide for solid reagent deposition patterns that facilitate uniform reconstitution. The reagent may be deposited in a parabolic pattern mirroring the flow pattern of the fluid front in a wide, narrow channel, thereby increasing the likelihood of uniform exposure of the sample contents to the reagent. The selection of sheets of dried reagents, layers of reagents, or individual spot arrays depends on the desired reconstitution event, the rate of reconstitution, and on whether additional mixing is employed.

For reagent spot arrays, ink-jet printing and piezocoupled micropipette tips can dispense drops of liquid reagent in a variety of uniform or non-uniform patterns on the surface of an active region, and deposition of separate reagents in separate areas of the active region can be achieved if sequential modification of the fluid sample is desired, or if combined reagents cannot be dried as a single reagent. If the active region is a high surface-to-volume ratio structure, the region may be dipped into, sprayed with, or otherwise exposed to, a reagent, and dried before incorporation into the cartridge.

The operations enabled by specific chemical interactions include specimen volume dilution; pH adjustment; biochemical solubilization; molecular aggregation; cellular or viral lysis; agglutination of target cells or capture-particles; filtration; neutralization; specific analyte extraction and purification; contaminant extraction and separation; precipitation of specific molecules; binding of analyte to reporter moieties; and dried reagent reconstitution.

The overall geometry of the cartridge may take a number of forms. For example, the cartridge may incorporate a plurality of interactive regions, e.g. channels or chambers, and storage regions, arranged in series, so that a fluid sample is moved serially through the regions, and the respective operations performed in these regions. Alternatively, the cartridge may incorporate a central fluid interactive region connected to peripheral reagent or diluent storage chambers.

Generally, a single cartridge includes at least two distinct interactive regions, and preferably, at least three or more distinct interactive regions. Individual regions and regions may vary in size and shape according to the specific function of the region or region. In some cases, elongated or spherical interactive regions or chambers may be employed. In general, the interactive regions may vary in dimensions from microscale (microns) to mesoscale (submillimeters) to macroscale (millimeters).

In some cases, a separate region may be used as a volumetric region, e.g., to precisely measure fluid volumes for introduction into an adjacent region. In such cases, the volume of the region is dictated by volumetric needs of a given reaction. Further, the cartridge may be fabricated to include a series of regions having varied dimensions and volumes in comparison to each other.

Cross-sectional areas of the regions dictate the fluid resistance, pressure, and volumetric flow rates. The regions have dimensions or properties (e.g., internal diameter, surface friction, materials, embedded chips, temperature, or other factors) that precisely control the volumetric flow rate, dwell times in the regions, processing efficiencies of on-board, prepackaged reagents, and efficiencies of sensors and detectors. Consequently, precise dwell times, reagent reconstitution rates, flow rates, flow directions, and all of the flow-through elements and parameters may be implemented.

The cartridge may be fabricated using one or more of a variety of methods and materials suitable for microfabrication techniques. For example, in preferred aspects, the cartridge may comprise a number of planar members that may individually be sheets or injection molded parts fabricated from a variety of polymeric materials, or may be silicon, glass, or the like. In the case of substrates like silica, glass or silicon, methods for etching, milling, drilling, etc., may be used to produce wells and depressions which make up the various regions, chambers and fluid channels within the cartridge capable of receiving inserts such as pouches, chips, papers, beads, gels, porous materials, tablets, and the like.

Microfabrication techniques, such as those regularly used in the semiconductor and microelectronics industries, are particularly suited to these materials and methods. These techniques include, e.g., electrodeposition, low-pressure vapor deposition, glass bonding, photolithography, wet chemical etching, reactive ion etching (RIE), laser drilling, and the like. Where these methods are used, it will generally be desirable to fabricate the planar members of the cartridge from materials similar to those used in the semiconductor industry, i.e., silica glass, silicon, gallium arsenide, polyimides, metal films and the like. In additional embodiments, the cartridge may comprise a combination of materials and manufacturing techniques described above. In some cases, the cartridge may include some parts of injection molded plastics, and the like, while other portions of the body may comprise etched glass or silicon members, and the like.

The cartridge may also incorporate one or more filters for capturing sample components, e.g., cells, spores, or microorganisms to be lysed. The filters may also be used for removing particulates, cell debris, and protein solids from the sample. The filters may be within any region, e.g., within the fluid passages or channels leading between regions or within a particular interactive region. A variety of filter media may be used, including, e.g., cellulose, nitrocellulose, polysulfone, nylon, vinyl copolymers, glass fiber, micromachined structures, and the like. Similarly, separation media, e.g., ion exchange resins, affinity resins or the like, may be included within the cartridge.

The surfaces of the fluid interactive regions that contact the fluid sample and reagents may be made hydrophobic or hydrophilic depending upon the particular application. Where reagents involved in a particular analysis are incompatible with the materials used to manufacture the cartridge, e.g., silicon, glass or polymeric parts, a variety of coatings may be applied to the surfaces of these parts that contact the reagents. For example, components that have silicon elements may be coated with a silicon nitride layer or a metallic layer of, e.g., gold or nickel, sputtered or plated on the surface to avoid adverse reactions with these reagents.

Similarly, inert polymer coatings, Parylene® coatings, or surface silanation modifications may also be applied to internal surfaces of the cartridge in order to make the overall system more compatible with the reactions being carried out. For example, in the case of nucleic acid analysis, it may be desirable to coat the surfaces with, e.g., a non-stick coating to prevent adhesion of nucleic acids to the surface. Additionally, patterned metal electrical conductors for activating actuators, heaters, sensors, and the like may be used. Such conductors may be coated with insulator coatings in those instances where electrical leads are placed in contact with fluids, to prevent shorting out or gas formation from electrolysis. Such insulators are well known in the art, e.g. screen-printed polymers, epoxies, ceramics and the like.

Although the preferred embodiment incorporates flow controllers, e.g. valves, it is possible for a continuously-flowing fluid stream to be guided, divided and diverted to various regions within the cartridge without the incorporation of valves. In one embodiment, the fluid stream flows down a channel with relatively little flow resistance into a second region, e.g., a waste chamber. The waste chamber may be vented through a port blocked with a hydrophobic porous membrane, such as Goretex®. When the waste chamber is filled, and all the air in the waste chamber is expelled through the membrane vent, the fluid sample cannot pass through the membrane, and a back-pressure is developed.

The back-pressure is sufficiently large to force the remaining fluid stream through a smaller, secondary, capillary channel, pressure sensitive filter, or other flow restrictor located upstream from the first chamber. Once fluid flow is initiated through the small channel, no additional fluid will flow into the first channel and the fluid stream will be completely diverted into the secondary channel. Optionally, the smaller channel may be locally heated to induce diversion of the flowing sample into the smaller channel before the larger region or chamber is full.

Figure 4:
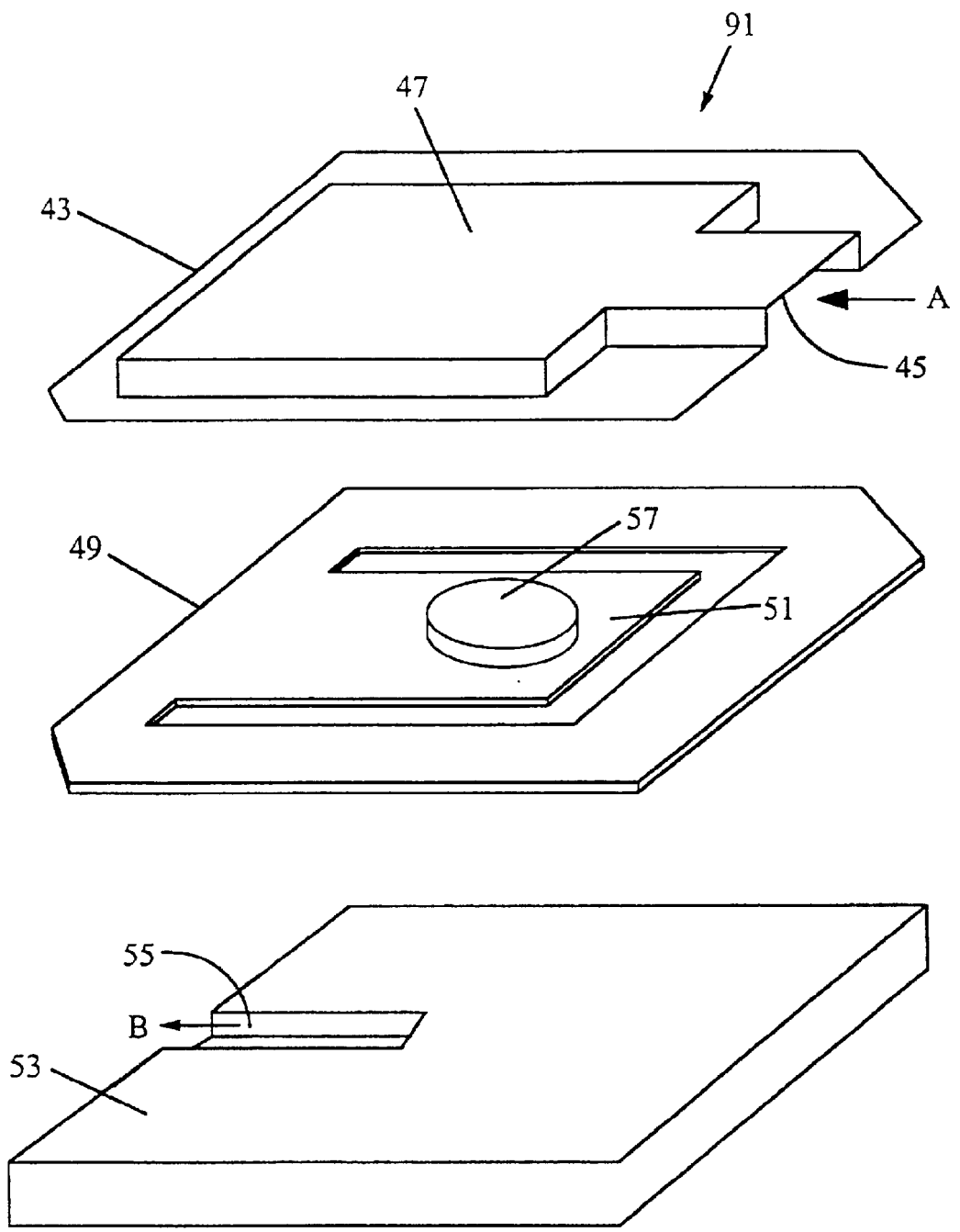
FIG. 4 is an exploded view of a fluid diode for the prevention of backflow.

In addition, fluid may be prevented from flowing back upstream by fluid diodes. FIG. 4 shows one example of such a fluid diode. Fluid is permitted to flow in a direction from A to B, but prevented from flowing in the opposite direction from B to A. The diode 91 comprises a top portion 43 having a port 45 and an adjoining recess 47; a flex circuit plate 49 having a flap 51; and a bottom portion 53 having a channel 55. When the diode 91 is deactivated, a magnetic disc 57 on the flap 51 is attracted towards the top portion 43 by an external magnetic force provided by, e.g., the external instrument. The flap is biased against the recess 47 in the top portion 43, thus allowing fluid flowing through the port 45 to pass beneath the flap 51 and through the channel 55 of the bottom portion 53.

When the diode 91 is activated, the magnetic force is disabled and the flap 51 returns to a sealing position due to the spring constant of the flap which prevents fluid from passing from the port 45 beneath the flap 51 and through the channel 55. In this manner, fluid present in the bottom portion 53 is prevented from flowing backwards through the port 45 of the top portion.

The cartridge preferably has a venting element to release back pressure of fluids. The vent may include an opening to the external environment (e.g. inlet port or outlet port with or without a hydrophobic vent). Conveniently, the vent may be an internal expandable cavity such as a corrugated membrane or an elastic latex membrane. Release of fluids through the vent may be passive or active, as in the application of a vacuum to a port on the cartridge.

The inclusion of gas permeable fluid barriers, e.g., poorly wetting filter plugs or hydrophobic membranes, in the cartridges also may be used to create a fluid direction and control system. Such filter plugs, when incorporated at the end of a chemically interactive region opposite a fluid inlet, allow air or other gas present in the interactive region to be expelled during introduction of the liquid component into the region. Upon filling of the region, the fluid sample contacts the hydrophobic plug thus stopping net liquid flow. Fluidic resistance may also be employed as a gas permeable barrier to accomplish this same result, e.g., using fluid passages that are sufficiently narrow to provide an excessive resistance, thereby effectively stopping or retarding liquid flow while permitting air or gas flow.

A variety of materials are suitable for use as poorly wetting or gas permeable filter plugs including, e.g., porous hydrophobic polymer materials, such as spun fibers of acrylic, polycarbonate, Teflon®, pressed polypropylene fibers, or any number of commercially available filter plugs. Alternatively, a hydrophobic membrane can be bonded over a through-hole to supply a similar structure. Modified acrylic copolymer membranes are commercially available from, e.g., Gelman Sciences (Ann Arbor, Mich.) and particle-track etched polycarbonate membranes are available from Poretics, Inc. (Livermore, Calif.). Venting of heated chambers may incorporate barriers to evaporation of the sample, e.g., a reflux chamber. Excessive evaporation of fluid from the sample may be prevented by disposing a mineral oil layer within the chamber and over the top surface of the sample to permit the evolution of gas while controlling evaporation.

Lysing regions within the cartridge can be designed to effect lysing of target cells by physical, chemical or other means, or a combination of such means. Physical means includes the mechanical disruption of the cells, such as by the vibration of glass or plastic beads or other particles or by impacting the target cells or viruses onto sharp microstructures. Thermal energy transfer, such as by heating a virus suspension to 95° C. or by repeated freeze-thawing of activated bacterial spores to disrupt cell walls, may also be used.

Chemical lysing can be employed alone or in combination with physical or ultrasonic lysing. Typical chemical lysing agents fall into several categories, such as enzymes, detergents, and chaotropes. Lysosyme is an enzyme that hydrolytically attacks the cell walls of many bacteria; trypsin is a protease enzyme that breaks the cell membrane of most eukaryotic cells. Other proteases with specificity for certain peptide sequences can be employed and are preferred if the target moiety is liable to certain proteases. Proteinase K is often used because it also digests nuclear proteins and host cell enzymes that may interfere with polymerase chain reaction (PCR). For eucaryotic cells, detergents such as Triton X-100 or sodium dodecyl sulfate solubilize the cell membrane and release intracellular contents. Chaotropes such as guanidine isothiocyanate or urea can be used to lyse cells and have the additional benefit of inhibiting RNAses that can destroy target RNA.

The mechanical disruption of target cells or viruses can be accomplished with interactive regions designed to tear the surface membrane or cell wall of the target organism via shearing or vibration. Vibration can be accomplished by containing glass or other beads in a chamber, and by coupling to the chamber a piezomembrane also incorporated into the cartridge. Alternatively, an ultrasonic transducer, such as an ultrasonic horn, may be coupled to a wall of the chamber to transfer ultrasonic energy to the cells. The frequency and amplitude of the ultrasound is tuned to correspond with the resonant frequency of the target cells and optimized to effect lysis with minimal heating or cavitation, though the latter may be required for efficient lysis.

Microfabricated chips can be designed to effect one or more modes of physical or chemical disruption of host cell walls or membranes. In one embodiment, the chip has an integral heater and high surface area microstructures derivitized with amino-silane to allow the chemical conjugation of antibodies with specificity and avidity for the surface proteins of a target cell or virus. When a fluid sample containing the target cell or virus flows through the chip, the target cell or virus is bound by antibodies linked to the high-surface area microstructures and removed from the flowing fluid stream. The microstructures are heated to 95° C. at a later time causing the viruses to lyse.

Other methods of cell extraction may also be used, e.g., employing a channel with restricted cross-sectional dimensions so that shear stress causes cell lysis when the sample is passed through the channel at sufficiently high pressure. Alternatively, cell extraction and denaturing of contaminating proteins may be carried out by applying an alternating electrical current to the sample. Numerous other methods may be utilized within the cartridge to effect lysis and extraction. Following extraction, it will often be desirable to separate the nucleic acids from other elements of the crude extract, e.g., denatured proteins, cell membrane particles, and salts. Removal of particulate matter is generally accomplished by filtration, flocculation and the like. A variety of filter types may be readily incorporated into the chemically and/or mechanically interactive regions of the cartridge. Further, where chemical denaturing methods are used, it may be desirable to desalt the sample prior to proceeding to the next step. Desalting of the sample and isolation of the nucleic acid may be carried out, e.g., by binding the nucleic acids to a solid phase and washing away the contaminating salts, or by performing gel filtration chromatography on the sample, by passing salts through dialysis membranes, and the like. Suitable solid supports for nucleic acid binding include, e.g., filters, beads, fibers, membranes, glass wool, filter paper, polymers, and gel exclusion media.

In some embodiments, enzymes, such as a polymerase enzyme, may be present within an amplification region, coupled to a suitable solid support, or to the walls and surfaces of the region. Suitable solid supports include those that are well known in the art, e.g., agarose, cellulose, silica, divinylbenzene, polystyrene, etc. Coupling of enzymes to solid supports has been reported to impart stability to the enzyme in question, which allows for storage of days, weeks or even months without a substantial loss in enzyme activity, and without the necessity of lyophilizing the enzyme. Monoclonal antibodies are available which bind the enzyme without affecting its polymerase activity. Consequently, covalent attachment of the active polymerase enzyme to a solid support, or the walls of the amplification region may be carried out by using the antibody as a linker between the enzyme and the support.

In another aspect of the invention, ligand binding methods can be used in the cartridges for binding and capturing specific cell types and/or other analytes. Ligand binding entities, such as nucleic acids and proteins, may be located at selected capture regions, attached to the surface(s) of the analyte capture components, to form a specific analyte-reacting region. Ligand coupling chemistries, such as silane-based chemistries, may be used. Homo- or hetero-bifunctional linkers, with one functionality binding to the internal surface and the other to a target in the test sample, may be employed. A sample containing the target analyte is passed continuously through the cartridge and the analyte binds to the ligand covered surface. After subsequent washing with one or more wash solutions, the ligand-analyte complexes can be eluted. Alternatively, a secondary anti-analyte molecule conjugated to a reporter molecule may be passed through the cartridge, so that the conjugate is captured by the analyte. This complex may also be eluted.

In particularly preferred embodiments, the cartridge is made from at least one injection molded, press molded or machined polymeric part that has one or more wells or depressions manufactured into its surface to define several of the walls of the interactive regions. Examples of suitable polymers for injection molding or machining include, e.g., polycarbonate, polystyrene, polypropylene, polyethylene, acrylic, and commercial polymers such as Kapton®, Valox®, Teflon®, ABS, Delrin® and the like. A second part that is complementary in shape is mated to the surface of the first part to define the remaining wall of the cartridge. The mating part or a third part may be a printed circuit board for implementing electrical contact directly with the fluid or indirectly via the cartridge.

The cartridge may be fabricated in such a way that specific regions or regions interact with an external instrument via exchange of electromagnetic radiation. Many plastics commonly used for such cartridges (e.g. polypropylene and polycarbonate) are optically transparent. In general, insulating materials allow electromagnetic radiation to pass over a wide frequency range. Such radiation may be of any frequency consistent with the intended application. For example, radio waves may be used as an alternative means of communicating with the cartridge. Radio waves may also be used to supply small amounts of power to any internal circuitry within the cartridge. Microwave frequencies may be used to induce heating of the fluid sample. Infrared signals may be used for heating, or for data exchange via an IR link, similar to those used in personal computers.

Optical frequencies, using light emitting diodes (LEDs) and photodetectors, such as photodiodes, are useful for detection of fluid presence (by detecting changes in optical transmittance), and for monitoring of chemical reactions (by, e.g., measuring absorption, fluorescence, or luminescence at specific wave lengths). Optical, as well as ultraviolet frequencies may be used to excite fluorescence of reaction products for detection. These frequencies may also be used to induce or accelerate chemical reactions.

Higher frequency radiation, such as deep UV or x-ray radiation, is also possible for specific applications, although the sources for these types of radiation may not always be practical in a small instrument. Sources of ionizing radiation (such as radioactive materials) could be reasonably incorporated into an instrument, and such radiation used for specific purposes within the cartridge, such as the enhancement of reactions or detection of specific fluid components or properties.

The cartridge may be fabricated in such a way that specific regions or regions may interact with the external environment via magnetic forces. For example, a region of the cartridge may contain a reservoir of magnetic beads. Such beads can be functionalized with various binding agents. By applying a series of magnetic fields to the cartridge (e.g. by means of switchable electromagnets) these beads may be vibrated or moved from one region to another. Using AC electromagnetic fields, such beads may be caused to circulate within a small region of the cartridge to mix fluids within the cartridge.

Magnetic forces may also be used to operate small valves within the cartridge for fluid control. A small strip of magnetic material may be incorporated into the cartridge to divert the fluid flow along one particular flow path. Another possibility is to fabricate the magnetic strip in such a way that it returns to the first position when the field is removed. The strip could be fabricated in such a way as to be mechanically bistable. Application of a magnetic pulse to the strip causes a mechanical transition from the initial bistable state to the second state. In this second state, the strip diverts the fluid flow to an alternative path. An array of such valves allows complete control of the fluid motion.

The cartridge may be fabricated so that specific regions may interact with the external instrument via electric fields. By fabricating very thin regions within the cartridge, and by mating these with corresponding conductive areas within the instrument, electric fields may be applied to the fluid without the need for any electrical connections to the cartridge itself.

Such electric fields may be used to move charged molecules from one surface to the other within the cartridge. By proper design of the fluidic paths, such a configuration may be used to separate charged from uncharged molecules, or to attract and hold charged molecules while other unwanted molecules are flushed from the system.

A number of the operations performed by the various interactive regions of the cartridge require a controllable temperature. For example, PCR amplification requires cycling of the sample among a strand separation temperature, an annealing reaction temperature, and an extension reaction temperature. A number of other reactions, including isothermal DNA amplification techniques, ligand binding, enzymatic reactions, extension, transcription and hybridization reactions are also generally carried out at optimized, controlled temperatures.

Temperature control is generally supplied by resistive heaters which are prepared using methods that are well known in the art. For example, these heaters may be fabricated from thin metal films applied within or adjacent to channels or chambers using well known methods such as sputtering, controlled vapor deposition, screen printing and the like. The heater is electrically connected to a power source which delivers a current across the heater. The electrical connections may be fabricated using methods similar to those described for the heaters.

In one embodiment, a controllable heater is disposed within or adjacent to a region for thermal control of the sample. Thermal control is carried out by varying the current supplied to the heater to achieve the desired temperature for the particular stage of the reaction. Alternatively, thermal control may be achieved by transferring the fluid sample among a number of different reaction regions or regions of the same cartridge, having different, constant temperatures, or by flowing the sample through a serpentine channel which travels through a number of varied temperature zones. Heating may alternatively be supplied by exposing the region to a laser or other radiation source.

Resistive heater elements may also be incorporated into regions of the cartridges by diffusing silicon into the regions or by depositing thin-film metal, carbon, or polysilicon at selected regions. Controlled heating provides additional functional capabilities, such as mixing, dissolution of solid reagents, lysing, thermal denaturation of proteins and nucleic acids and lysis of cells, elution of bound molecules, enhanced diffusion rates of molecules in the sample, and modification of surface binding coefficients, as well as high efficiency thermal cycling for polymerase and ligase chain reactions. Cooling features may also be exploited in high surface area regions, for example, with external cooling fins.

Preferably, the heaters are capable of producing temperatures in excess of 100° C. without suffering adverse effects as a result of the heating. The heaters may be provided as a layer on one surface of an interactive region or other region, or may be provided as molded or machined inserts for incorporation into a region or region. Control of the power source is typically carried out by an appropriately programmed processor, such as the processor in the external instrument. The heaters may be incorporated within the cartridge by depositing a resistive conductive film or insert on a surface of the cartridge, or alternatively, the heaters may be provided exteranally, e.g. in the instrument, and applied to the exterior of the cartridge, adjacent to a particular region, so that heat is conducted into the region.

Temperature controlled regions may also include miniature temperature sensors for monitoring temperatures and thereby controlling the application of current across the heater. A wide variety of microsensors are available for determining temperatures, including, e.g., thermocouples having a bimetallic junction which produces a temperature dependent electromotive force (EMF), resistance thermometers which include material having an electrical resistance proportional to the temperature of the material, thermistors, IC temperature sensors, quartz thermometers and the like. Alternatively, the temperature coefficient of resistance of the heater itself may be monitored to control the heat input.

The temperature measured by the temperature sensor and the input for the power source will typically be input to a processor, e.g. a microprocessor or microcontroller in the external instrument, which is programmed to receive and record this data. The same processor will typically include programming for instructing the delivery of appropriate current for raising and lowering the temperature of the interactive region or regions. For example, the processor may be programmed to take the interactive region through any number of predetermined time/temperature profiles, e.g., thermal cycling for PCR, and the like. Given the small size of the cartridges of the invention, cooling of an interactive region will typically occur through exposure to ambient temperature. However, additional cooling elements may be included if desired, e.g., coolant systems, Peltier coolers, water baths, heat pipes, and the like.

In alternate aspects, mixing may be accomplished by the incorporation of ferromagnetic elements within the cartridge which may be vibrated by supplying an alternating current to a coil adjacent the device. The oscillating current creates an oscillating magnetic field through the center of the coil which results in vibratory motion and rotation of the magnetic particles in the cartridge and mixing of the fluid components. In addition to sensors for monitoring temperature, the cartridge may contain sensors to monitor the progress of one or more of the operations of the device. For example, optical sensors and pressure sensors may be incorporated into one or more regions to monitor the progress of the various reactions, or within flow channels to monitor the progress of fluids or detect characteristics of the fluids, e.g., pH, temperature, electrical conductance, capacitance, fluorescence, viscosity, (chemi)luminescence, color, and the like.

The cartridge will typically include temperature sensors and controllers. For example, a heating element or temperature control block may be disposed adjacent the external surface of a chemically interactive region to transfer heat to the region. In this case, preferred cartridges include a thin external wall for regions in which thermal control is desired. This thin wall may be a thin cover element, e.g., polycarbonate sheet, or high temperature tape, i.e. silicone adhesive on Kapton® tape (commercially available from, e.g., 3M Corp). In one embodiment, the cartridge may comprise two or more components that are fabricated separately, and then bonded together. Some surfaces of the components ultimately become the interior of the fluid flow regions or channels.

On such surfaces, conductive layers may be deposited. These could be one of several metals, for example gold, chrome, platinum, silver, carbon, copper or other metals, deposited by standard thin film deposition techniques such as plating, evaporation or sputtering. Another method for deposition of such conductive materials is via thick film technology. In this method, conductive pastes or inks are deposited by screen printing, and then baked to drive off solvents and leave behind the final conductor. Finally, thin films of carbon are commonly used for low cost conductive materials. These can also be screen printed and baked at low temperatures to form conductive layers.

Any of the above methods are useful for allowing conduction of electrical signals from the external environment, through the fluid seal area, and into the interior of the cartridge. These conductors can be made very thin, limited only by the necessary conductivity. In the case of a cartridge, the thickness of the conductors may be on the order of 0.0254 mm.

Electrical signals through such conductors may be used in a number of ways, both as inputs to the cartridge and as outputs from it. Some signals involve making a circuit, part of which is the fluid itself within the cartridge. In one embodiment, such a circuit is used simply to sense the presence or absence of the fluid. Two conductive terminals are routed to regions within the fluid channel, close to one another but not connected to each other. External electronics monitors the impedance between these conductors, by, for example, applying a small voltage between them and monitoring the current flow. When no fluid is present, the impedance will be very high. However, when fluid passes this point in the channel, the fluid will bridge the gap between the two terminals. Since the fluids typically used in biological and chemical applications are at least mildly conductive, this fluid will cause the impedance in the circuit to decrease dramatically. This decrease in impedance can be sensed by the electronics, and decisions made based on this input. By placing several such circuits along the length of any fluid channel, the external electronics may be used to monitor the fluid velocity, thus monitoring the progress of the intended fluidic processing.

Electrodes in contact with the fluid might also be used for monitoring specific characteristics of the fluid. Capacitance, fluid conductivity, fluid pH, capacitance, reaction region humidity (e.g. in paper based cartridges) are all examples of specific fluid parameters that might be monitored by electronic means. Specific electrode configurations are also possible to allow electrochemical detection of reaction products.

Another example is the use of such electrical connections into the fluid for manipulation of biomolecules such as DNA. Such molecules can be moved through fluids by DC electrophoresis. In this case, one electrode makes contact with the fluid as a counter electrode. Many other electrodes can be biased with respect to the counter electrode to attract charged molecules. For example, some macromolecules such as DNA are negatively charged. By biasing electrodes positively with respect to the counter electrode, these macromolecules can be attracted to the positive electrodes. This may be useful for isolating such molecules from other fluidic components, or for attracting such molecules to specific reaction regions within the cartridge.

Another electronic technique useful for movement and isolation of biomolecules is AC dielectrophoresis. In this case, two or more electrodes are typically configured close to one another, and in a physical configuration which yields non-uniform electric fields. AC fields at frequencies up to tens of MHz are known to induce electrical polarization of such molecules, causing them to move, or be attracted to, regions where they may be isolated or further processed. Molecules also have unique signatures, i.e. particular molecules respond to a particular frequency of excitation. Thus specific molecules can be isolated from the fluidic sample by tuning of the frequency of the AC excitation. By using traveling wave excitation along a series of electrodes, these specific molecules can be moved from place to place.

Another application of an electrical connection is that of driving an electrolysis reaction to realize fluid movement. Electrical connections to a fluid reservoir could be used to realize an electrolytic pump (e-pump). In such a device, current is passed through a reservoir of electrolyte. This current causes gas evolution as the electrolyte solvent is decomposed into gases such as oxygen and hydrogen. These gases build up localized pressure and can serve as a motive source. This pressure can be transmitted to the process fluid within the cartridge through, e.g. a flexible membrane, thus realizing fluid motion of the fluid to be processed.

Figure 5A:
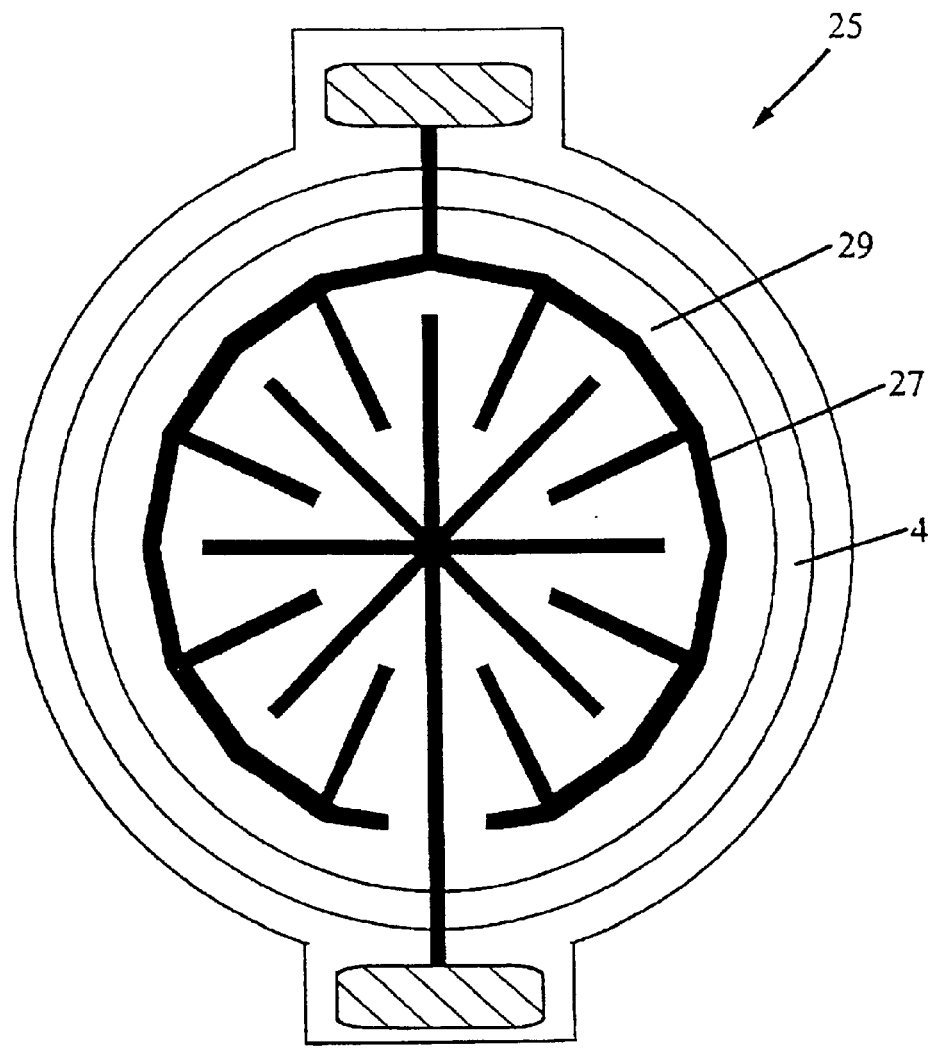
FIG. 5A is a schematic, plan view of an electrolytic pump.
Figure 5B:
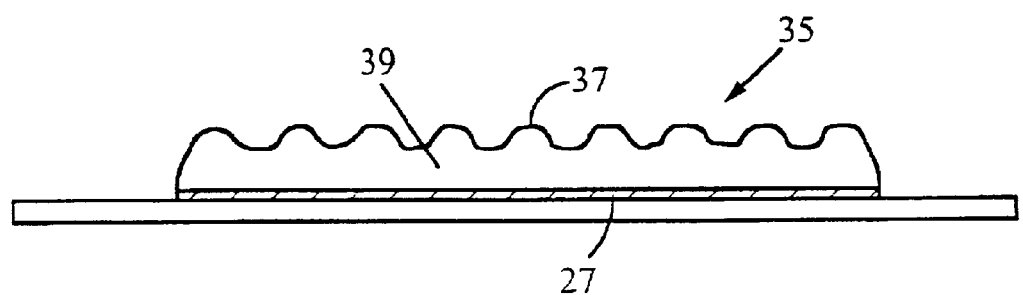
FIG. 5B is a schematic side view of the pump of FIG. 5A.

FIGS. 5A and 5B show one such electrolytic pump 25. As shown in the plan view of FIG. 5A, the pump 25 includes electrodes 27 having a star shape to assure that a current path is always available even after bubbles begin to form inside of the reservoir 29. A sealing ring 4 entraps electrolyte within the reservoir 29. As shown in the schematic side view of FIG. 5B, fluid 39 is contained within a pouch 35 having an expandable membrane 37. The fluid contacts electrodes 27 and decomposes when electric current is applied to the electrodes. The decomposing fluid creates a pressure build-up within the pouch 35. As the pouch expands due to increased pressure, the pouch biases against a liquid reagent pouch (not shown), thus forcing the liquid reagent contained within the liquid pouch to be released. By controlling the current (power) to the electrodes 27, and in conjunction with the aforementioned means for monitoring of fluid flow velocity, a closed loop fluid flow control system can be realized. Such an implementation opens up many possibilities for very well controlled reactions, as the fluid velocity (and hence residence times at various reaction regions) at various points in the processing cycle can be independently controlled and monitored.

Figure 6:
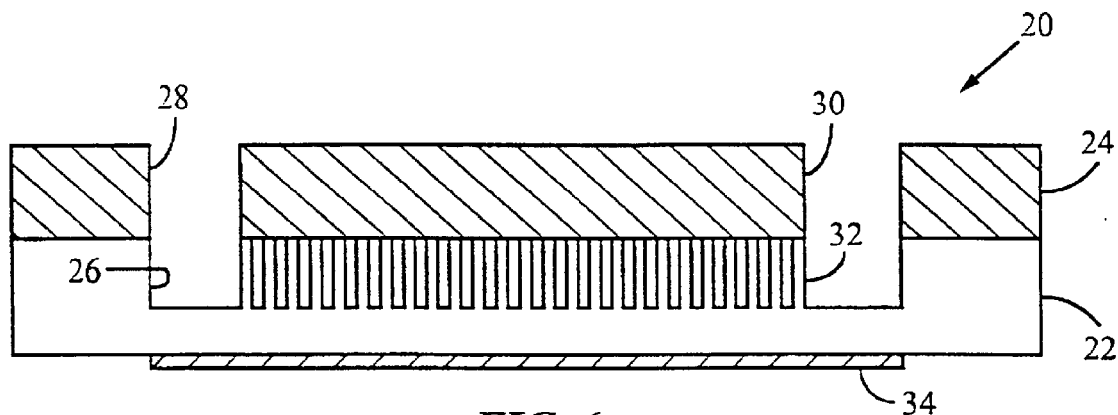
FIG. 6 is a schematic, cross sectional view of a flow-through chip for extracting analyte from a fluid sample according to a preferred embodiment of the invention.

FIG. 6 shows a schematic, cross sectional view of a preferred microfabricated chip 20 to be used as the flow through component in the cartridge of FIG. 2. The chip 20 is used to capture a desired analyte, e.g. nucleic acid, from a fluid sample and to provide a highly concentrated eluate of the analyte. The chip 20 includes a body having formed therein an inlet port 28, an outlet port 30, and an extraction chamber 26 for extracting the analyte from the fluid sample as the fluid sample flows through the body. The chamber 26 is in fluid communication with the inlet and outlet ports 28 and 30, and the ports are preferably positioned on opposite sides of the chamber 26 to permit continuous fluid flow through the chamber.

The body preferably comprises a base substrate 22 and a top substrate 24 bonded to the base substrate 22. The substrates 22 and 24 may comprise any suitable substrate materials, such as silicon, glass, silicon dioxide, plastics, or ceramics. In the preferred embodiment, the chamber 26 is formed in the base substrate 22, and the fluid ports 28 and 30 are formed in the top substrate 24. In alternative embodiments, however, many different configurations are possible, e.g., the chamber 26 may be partially or completely formed in the top substrate 24, the fluid ports may be formed in bottom or sides of the base substrate 22, etc. Several of these alternative embodiments will be described below.

The chamber 26 has internal attachment surfaces having sufficiently high surface area and binding affinity with the target analyte to capture the analyte as the fluid sample flows through the chamber. In the preferred embodiment, the internal attachment surfaces are formed by an array of internal microstructures, preferably high aspect ratio columns 32, integrally formed with a wall of the chamber 26 and extending into the chamber. For simplicity of illustration, only twenty-five columns are shown in the schematic view of FIG. 6. It is to be understood, however, that the chip of the present invention may include many more columns. In general, it is preferred to fabricate the chip with at least 100 columns, and more preferable to fabricate the chip with 1,000 to 10,000 columns. The number of columns depends, inter alia, on the amount and concentration of analyte in the sample, the dimensions of the chamber, the spacing of the columns, the flow rate of fluid through the chamber, etc. Specific techniques for fabricating the chip are described below.

Figure 8:
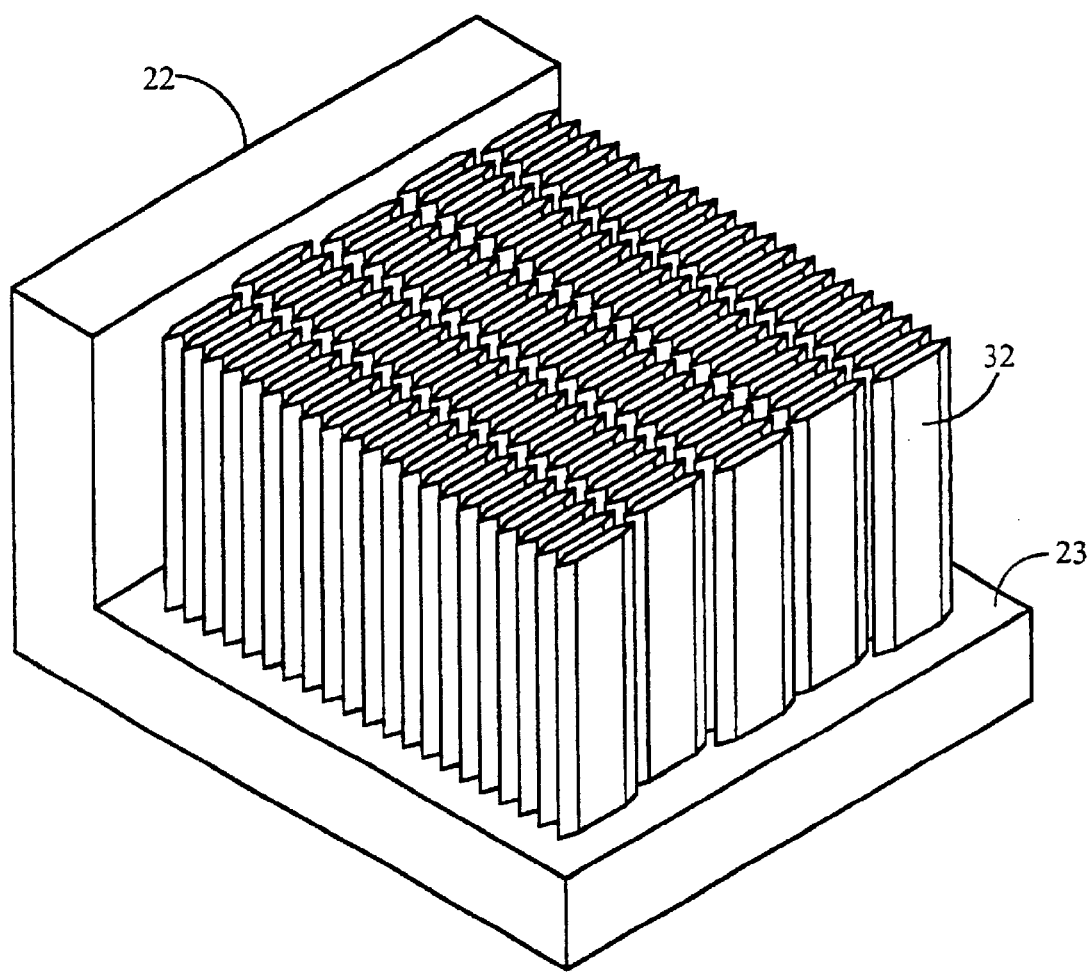
FIG. 8 is a three-dimensional view of microcolumns formed in an extraction chamber of the chip of FIG. 6.

FIG. 8 shows a portion of the array of columns 32 extending from a bottom wall 23 of the extraction chamber. The columns 32 preferably have an aspect ratio (ratio of height to width or diameter) of at least 2:1, and more preferably have an aspect ratio of at least 4:1. The high aspect ratio columns 32 provide a large surface area for capturing the analyte. As the fluid sample flows through the chamber, the analyte contacts and adheres to the surfaces of the columns 32. To elute the analyte, an elution fluid is forced to flow through the chamber, releasing the analyte, e.g. nucleic acid, from the surfaces of the columns 32 into the elution fluid. In the preferred embodiment, the columns 32 have a height equal to the depth of the extraction chamber, preferably at least 100 $\mu$m. In alternative embodiments, the extraction chamber may have a shallower depth, but depths of less than 100 $\mu$m may cause excessively slow fluid flow through the chamber.

Figure 9:
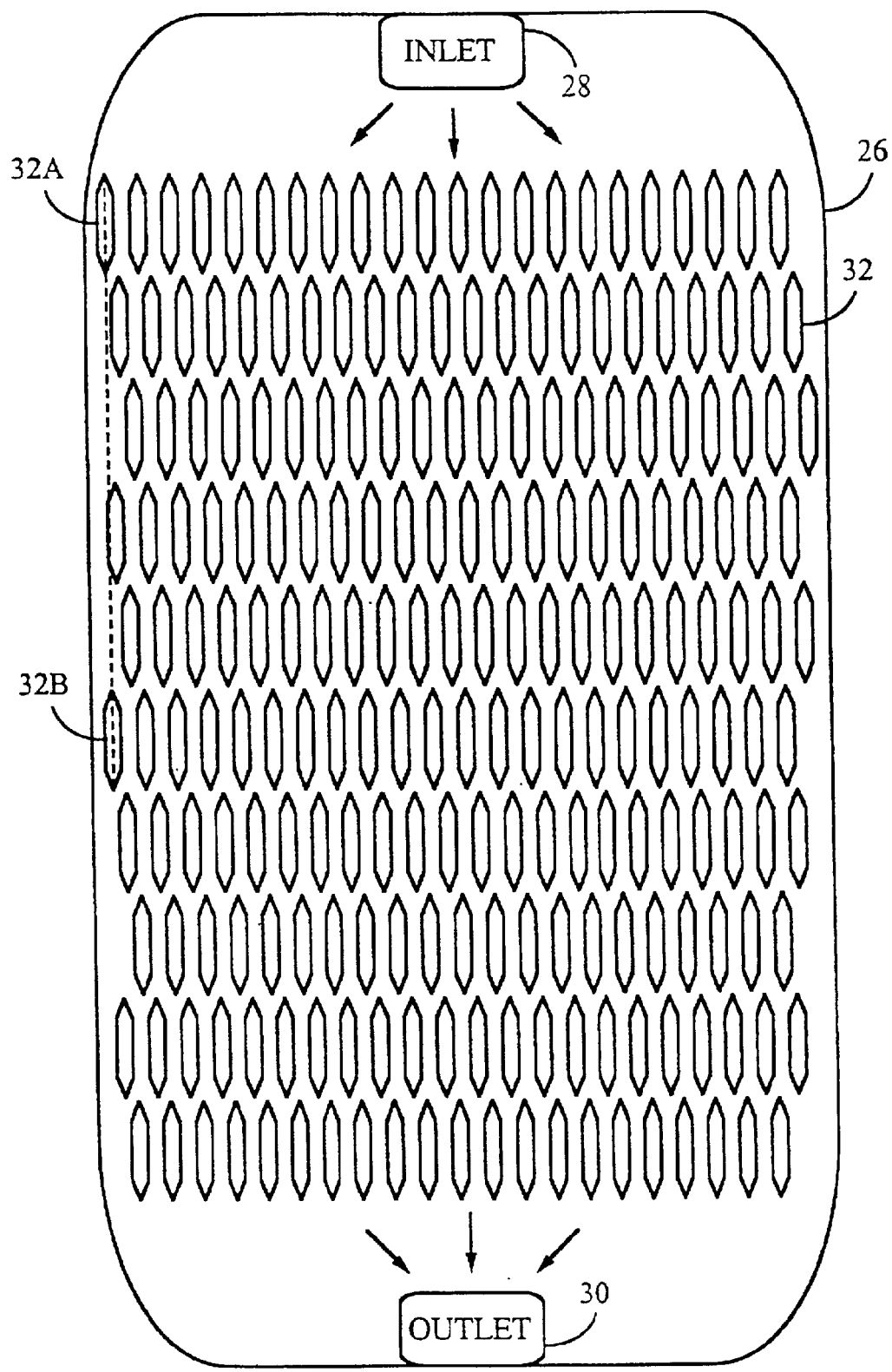
FIG. 9 is a schematic, plan view of the microcolumns in the chip of FIG. 6.

FIG. 9 shows a schematic view of the array of columns 32 disposed in the chamber 26. Fluid enters the chamber 26 through the inlet port 28 and flows between the columns 32 to the outlet port 30. The columns 32 are preferably arranged in an array that optimizes fluid interaction with the surfaces of the columns as the fluid flows through the chamber 26. The optimization of the column arrangement permits faster flow rates of fluids through the chamber without losing efficiency of extraction.

In the preferred embodiment, the columns 32 are disposed in rows, with each of the columns in a row spaced a uniform distance from adjacent columns in the row, i.e. the columns in a row preferably have uniform center to center spacing. For example, FIG. 9 illustrates ten horizontal rows of uniformly spaced columns 32. In addition, adjacent rows are preferably offset from each other such that the columns in each row are misaligned with the columns in an adjacent row. For example, each row of columns in FIG. 9 is offset horizontally from an adjacent row.

Also in the preferred embodiment, the rows are offset such that the columns in each row are misaligned with the columns in at least two previous and/or successive rows. The misalignment may be in a pattern of successive rows, where the chamber includes one pattern or a repeated pattern. For example, the pattern may repeat every three to ten rows. In the alternative, the misalignment of columns may be random from row to row.

Generally, any two adjacent rows in the array should not be offset from each other such that the columns in the first row are aligned exactly halfway between the columns in the second row. Instead, it is presently preferred to offset adjacent rows a distance greater than or less than 50% of the center to center spacing between the columns. This arrangement provides for an asymmetrically split flow pattern through the chamber to ensure that each branch of the fluid stream interacts as strongly as possible with the surfaces of the columns.

A specific example of a suitable arrangement of columns will now be given with reference to FIG. 9. In each row, the center to center spacing between adjacent columns is 15 $\mu$m. The columns are arranged in a pattern that repeats every five rows. In particular, each of the top five rows is offset 6 $\mu$m from a previous/and or successive row. The bottom five rows (the sixth through tenth rows) repeat the pattern of the top five rows, with the sixth row being aligned with the top row, e.g., column 32A is aligned with column 32B. Of course, this is just one example of a suitable array of columns and is not intended to limit the scope of the invention. It will be apparent to one skilled in the art from this description that the columns may be arranged in many other patterns, preferably within the general guidelines set forth above.

Figure 10:
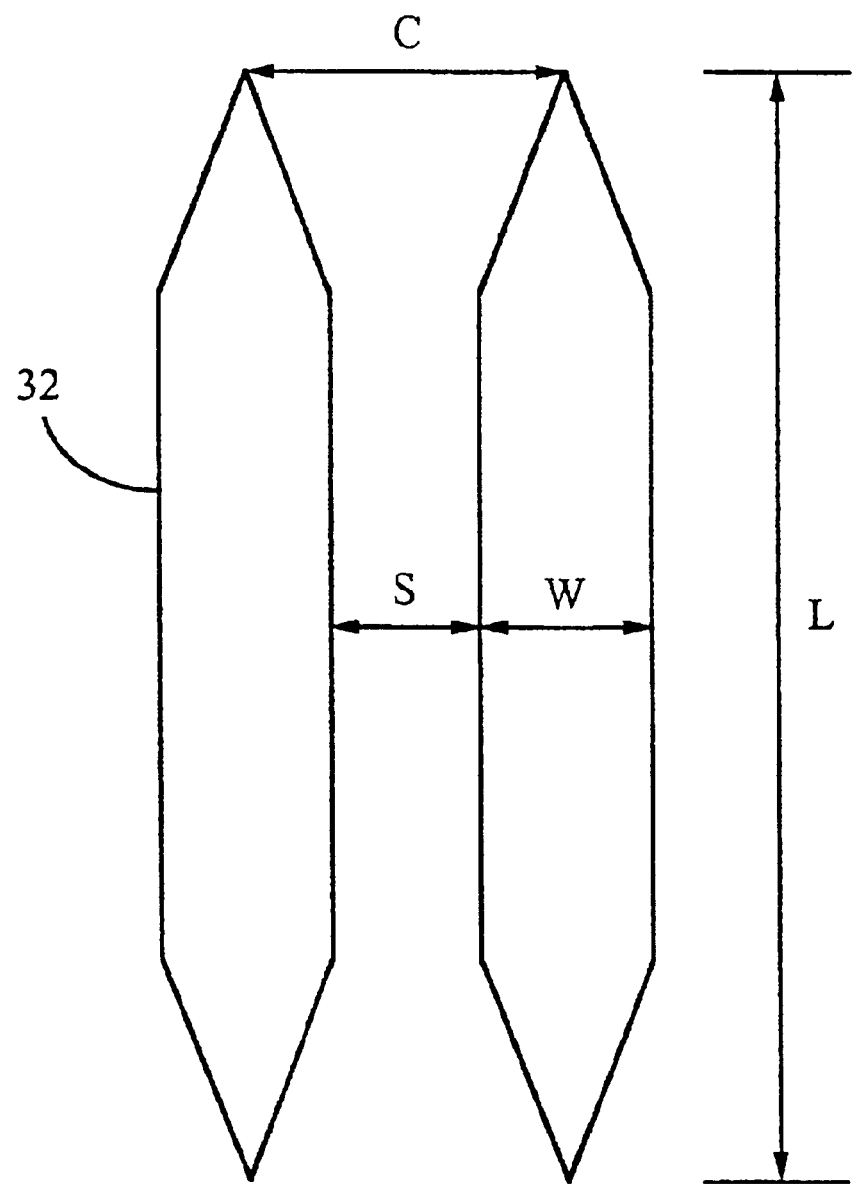
FIG. 10 is a plan view of two adjacent microcolumns in the chip of FIG. 6.

FIG. 10 shows a top plan view of two adjacent columns 32 in a row. The columns 32 preferably have a cross sectional shape and size which maximizes fluid contact with the surfaces of the columns while still allowing for smooth fluid flow through the chamber. In the preferred embodiment, this is achieved by fabricating columns having a long and thin cross sectional shape, preferably a streamlined shape, such as the hexagonal shapes shown in FIG. 10. In particular, each column 32 preferably has a ratio of cross sectional length L to cross sectional width W of at least 2:1, and more preferably of at least 4:1. Further, the cross sectional length L is preferably in the range of 2 to 200 $\mu$m, and the cross sectional width W is preferably in the range of 0.2 to 20 $\mu$m.

The gap distance S between adjacent columns in a row is preferably selected to be as small as possible while still allowing fluid to flow between the columns without excessive resistance. In general, the gap distance S may range from 0.2 to 200 $\mu$m, and more preferably, is in the range of 2 to 20 $\mu$m. The range of 2 to 20 $\mu$m is currently preferred because it provides for substantial fluid contact with the surfaces of the columns without causing excessive resistance to the fluid flow through the chamber. The center to center spacing C between adjacent columns in a row is the sum of the cross sectional width W and gap distance S, and is preferably in the range of 2.0 to 40 $\mu$m.

The length of the extraction chamber 26, its vertical dimension in FIG. 9, is preferably in the range of 100 to 5000 $\mu$, and more preferably at least 1000 $\mu$m. The width of the extraction chamber 26 is preferably in the range of 100 to 3000 $\mu$m. The fluid ports 28 and 30 each preferably have a width or diameter of at least 100 $\mu$m. It is presently preferred that the chamber 26 have a minimum length of 1000 $\mu$m to allow sufficient room for the array of columns 32 and for the fluid ports 28 and 30. In particular, it is presently preferred to confine the array of columns 32 to the center area of the chamber 26, leaving open space at the ends of the chamber 26 where the fluid ports 28 and 30 join the chamber. This arrangement increases uniformity of fluid flow into the chamber 26 prior to the fluid flowing between the columns 32.

Referring again to FIG. 6, the internal surfaces of the chamber 26, e.g. the columns 32 and chamber walls, may be coated with a substance having a high binding affinity with the target analyte. Suitable substances include, for example, silicon, silicon derivatives such as silicon dioxide, polymers, polymer derivatives such as polyamides, nucleic acids, certain metals, polypeptides, proteins, and polysaccharides.

The silicate ($SiO_2$) nature of glass can attract and bind nucleic acids. Silicon, when it becomes oxidized, results in a similar surface chemistry. Non-permanent (non-covalent) attachment (adsorption) to such a surface is typically based on weak dipole, hydrogen bonding, or ionic interactions between the surface and moiety to be captured. These interactions are reversible via changes in the ionic nature of the solvent and/or surface, heat, or other physiochemical means. Many materials can be tailored to have a variety of interactions with solvents and solutes in solution. Polymers can have active surface groups that provide specific interactive forces, and they can have copolymers or dopants that provide ionic or even hydrogen binding capabilities. Some polymers can have reversible polarities or adjustable conductivity. Synthetic and some natural polypeptides and proteins have shown a similar capability to have a variety of interactions with solute molecules. Metals, such as gold, are well known to have the ability to capture DNA, and due to its electronic nature, can change the ionic interactions with solutes.

The internal surfaces of the chamber 26 may also be coated with a substance having a high binding affinity with a specifically targeted analyte, e.g., a specific sequence of RNA from a virus or a specific sequence of DNA from a bacteria. This may be accomplished by coating the internal surfaces with a specific nucleic acid sequence complementary to the target nucleic acid sequence. The surfaces may be coated during manufacture of the chip or immediately prior to use.

The microfluidic chip 20 preferably includes a heater for heating the extraction chamber 26. The heater allows for highly efficient elution of the analyte from the chamber so that a large amount of analyte may be released into a small volume of elution fluid. The heater may also be used to facilitate capture of the analyte. One advantage of the use of a heater in a small volume microchamber is that minimal energy is required to heat the chip.

In general, the heater may comprise any suitable mechanism for heating the chamber 26, including resistive heaters, optical heaters for directing visible or infrared light, or electromagnetic heaters. If the body of the chip 20 is fabricated from an electrically conductive material, preferably silicon, the heater may simply comprise a power source and electrodes for applying a voltage across a portion of the body forming the chamber 26. Also, high thermal conductivity of the material allows for fast heating times, reduced power requirements, and highly uniform temperatures. This embodiment is described in greater detail below.

Figure 7:
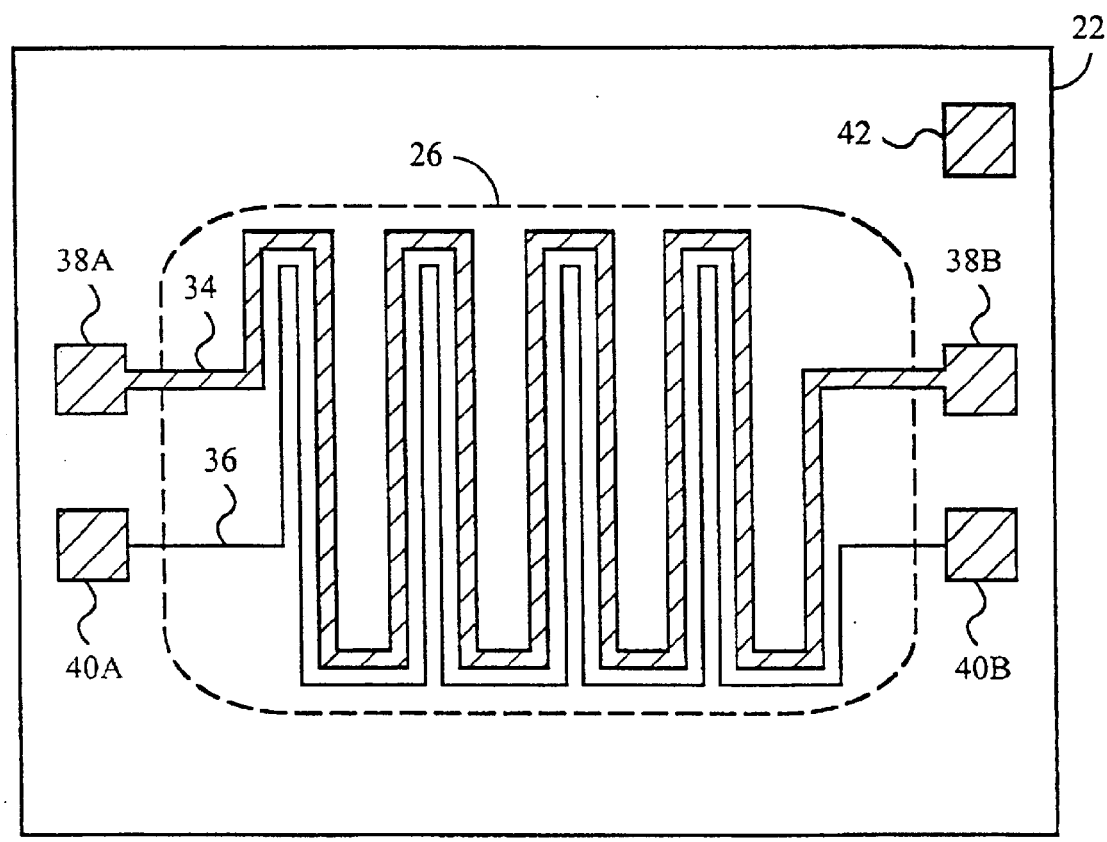
FIG. 7 is a bottom plan view of the chip of FIG. 6.

In the preferred embodiment, the heater comprises a resistive heating element 34 coupled to the bottom wall of the chamber 26. As shown in FIG. 7, the resistive heating element 34 is preferably a thin film of metal, carbon, or polysilicon that is patterned on the bottom surface of the substrate 22. Alternatively, the heating element may comprise a laminated heater source, such as an etched foil heating element, attached to the substrate 22. Electrically conductive bond pads 38A and 38B are also patterned on substrate 22 for electrically contacting opposite ends of the heating element 34.

The bond pads 38A and 38B may be connected by electrical leads to a power source for applying a voltage across the heating element 34. Control of the power source is preferably carried out by an appropriately programmed controller, such as a computer, microprocessor, or microcontroller in the cartridge or external instrument. The controller may be programmed to take the chamber 26 through any number of predetermined time/temperature profiles by varying the amount of power supplied to the heating element 34.

The microfluidic chip also preferably includes one or more temperature sensors in communication with the controller for measuring the temperature of the extraction chamber 26. In general, the temperature sensor may be any suitable device for measuring temperature, such as a thermocouple, resistance thermometer, thermistor, IC temperature sensor, quartz thermometer, or the like. Alternatively, the temperature coefficient of resistance of the heating element 34 may be utilized as a means to monitor the chamber temperature and to control the heat input by measuring the resistance as indicative of temperature.

In the preferred embodiment, the temperature sensor comprises a strip 36 of electrically conductive material patterned on the substrate 22. The strip 36 comprises a material having an electrical resistance dependent on the temperature of the material, so that the temperature of the chamber 26 may be monitored by monitoring the resistance of the strip 36. Electrically conductive bond pads 40A and 40B are also patterned on substrate 22 for electrically contacting opposite ends of the sensor strip 36.

In an alternative embodiment, the substrate 22 may also have an additional bond pad 42 patterned thereon for providing a bulk contact to the substrate 22. The bulk contact may be used to charge the internal attachment surfaces of the chamber 26 with a voltage to attract and/or elute nucleic acid. Suitable metals for forming the resistive heating element, sensor strip, and bond pads include aluminum, gold, silver, copper, and tungsten.

The bond pads 40A and 40B are connected by electrical leads to the controller, and the controller is preferably programmed to adjust the amount of power supplied to the heating element 34 in dependence upon the resistance of sensor strip 36. The controller, power source, heating element, and temperature sensor thus form a closed loop temperature control system for controlling the temperature of the chamber 26. Although a closed loop system is presently preferred, in alternative embodiments the temperature sensor may be eliminated and the chip may be operated in an open loop mode. Further, the processing electronics, including e.g., one or more microprocessors, multiplexers, power control circuitry, and sensor circuitry, may be included in the chip or located externally to the body of the chip and connected thereto.

The microfluidic chip is preferably used in combination with a cartridge, as previously described with reference to FIG. 2. One advantage of the flow-through chip is that it allows the analyte from a relatively large volume of fluid sample, e.g. several milliliters or more, to be concentrated into a much smaller volume of elution fluid, e.g., 25 $\mu$L or less. In particular, the ratio of the fluid sample volume forced to flow through the device to the volume capacity of the extraction chamber is preferably at least 2:1, and more preferably at least 10:1. In the preferred embodiment, the extraction chamber has a volume capacity in the range of 0.1 to 25 $\mu$L, and the volume of fluid sample forced to flow through the device is in the range of 1 to 100 mL, enabling concentration factors of 100 or greater.

Another advantage of the microfabricated chip is that it allows for rapid and direct heating of the internal attachment surfaces of the chamber. The integral nature and high thermal conductivity of the chamber walls and column structures allow for rapid heat transfer from the heating element directly to the attachment surfaces without necessitating heating of the fluid in the chamber. This improvement in efficiency is significant in terms of the speed, precision, and accuracy of the heating, as well as in the reduction in power required for the heating. In particular, the rapid and direct heating of the internal surfaces to which the analyte is bound greatly increases the degree and efficiency of the elution, and provides a significant improvement over prior art methods and devices.

A further advantage of the chip is that it includes an array of integrally formed microstructures, preferably high aspect ratio columns, which provide for a high degree of efficiency and control in separating analyte from a fluid sample. In addition to allowing direct and rapid heating of attachment surfaces, the microstructures greatly increase the effective surface area of the chamber which may be used to capture and elute analyte.

Further, with regularly spaced columns, the diffusion distances between the columns are consistent and there is uniformity of fluid flow so that every analyte is subjected to the same "micro-environment" as opposed to the random nature of beads and fibers. This uniformity allows for predictability of extraction parameters including the time required for each processing step, flow rates, heating amounts, fluid volumes, etc. In addition, the increased efficiency obtained by using an array of internal microstructures and by rapidly and directly heating attachment surfaces allows for the efficient extraction and elution of analytes with relatively high fluid flow rates through the chamber. This decreases the overall time required for the extraction and elution.

The microfabricated chips of the present invention are also useful for combinatorial synthesis of biopolymers such as oligonucleotides and polypeptides. Combinatorial synthesis allows very large numbers of sequences to be synthesized in a device by transporting, concentrating, and reacting monomers, coupling and deblocking reagents, and catalysts at separately addressable reaction/extraction microstructures. This use exploits the ability of the device to insulate selected microstructures from each other and from nearby reagents.

The chip 20 may be fabricated using a variety of techniques, including photolithography and/or micromachining. Fabrication is preferably carried out on silicon or other suitable substrate materials such as glass, silicon dioxide, plastics, or ceramics. A preferred method for fabricating the microfluidic device using deep reactive ion etching (DRIE) will now be described.

A 100 mm, n-type (100), 0.1 to 0.2 ohm-cm, double side polished silicon wafer is used as starting material for the base substrate 22. The wafer thickness is preferably in the range of 350 to 600 $\mu$m, depending on the desired structure. In one embodiment of making the chip, an ohmic contact may be made by using phosphorous ion implantation into a region in the backside, preferably to a depth of 0.2 to 5 $\mu$m. Alternatively, a p-type silicon wafer may be used, and the ohmic contact made using boron ion implantation. Implantation is followed by heating of the substrate to activate the dopant.

The wafer is then spun with photoresist (commercially available from, e.g., Shipley) on the frontside to obtain a photoresist thickness sufficient to mask the DRIE process. This thickness depends upon the final desired depth of the etch. The ratio of silicon etch rate to photoresist erosion rate is typically greater than 50:1. To etch structures that are 200 $\mu$m deep, 4 $\mu$m of photoresist is usually sufficient. The photoresist is softbaked at 90° C. for about 30 minutes, then exposed with the desired mask pattern, developed, and hardbaked using processes well known in the art of silicon wafer processing.

Figure 11:
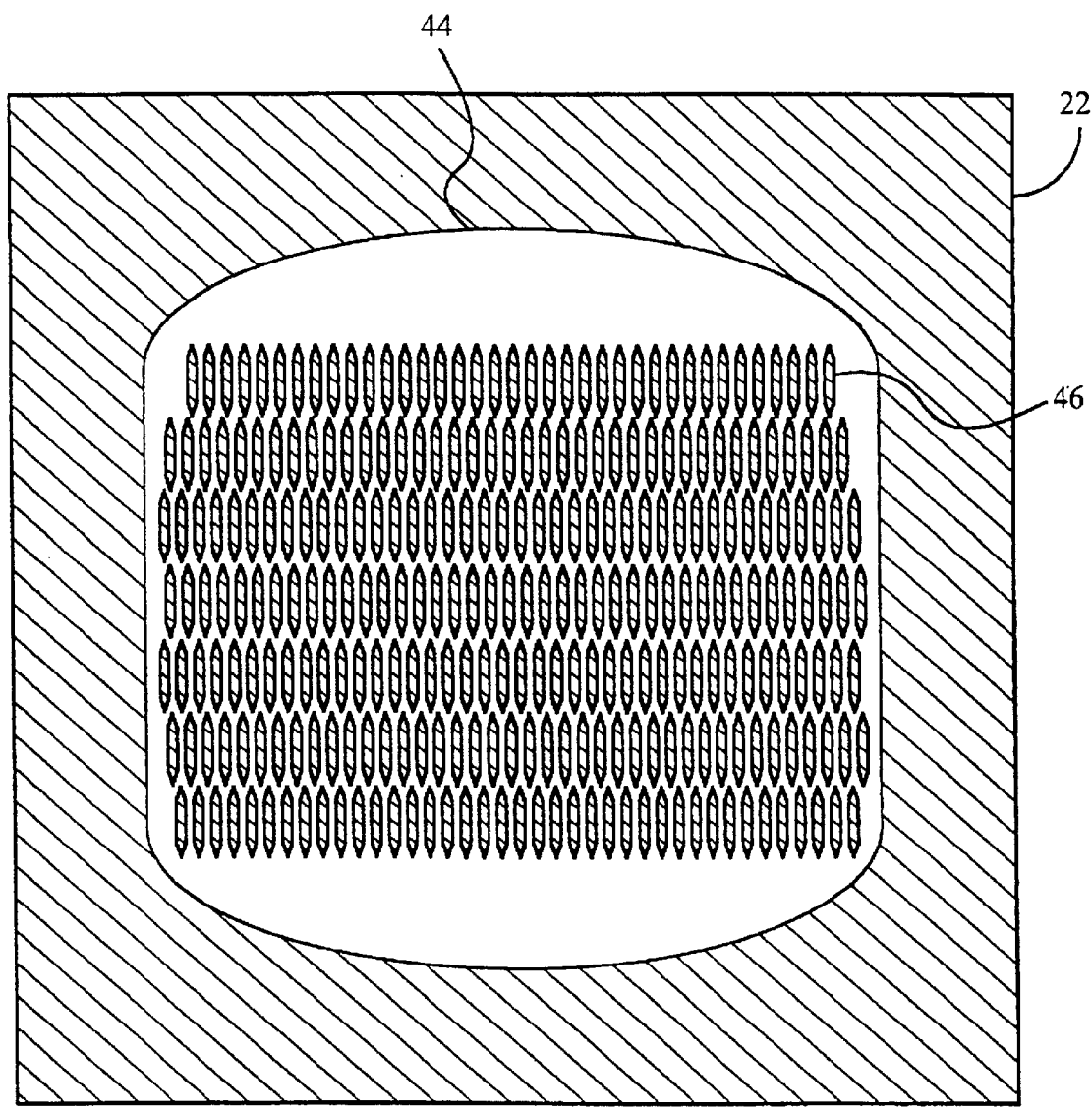
FIG. 11 is a schematic view of an etch mask defining a chamber pattern and a column pattern used in the fabrication of the chip of FIG. 6.

FIG. 11 illustrates a sample mask pattern on the frontside of the wafer. The etch mask defines a chamber pattern 44 for forming the extraction chamber in the substrate 22 and an array of column patterns 46 for forming a corresponding array of columns in the substrate. Due to space limitations in drawing size, the etch mask is illustrated with only several hundred column patterns 46. In the preferred embodiment, however, the array includes 1,000 to 10,000 column patterns for forming a corresponding number of columns in the substrate 22.

The patterned wafer is then etched using a DRIE process to form the extraction chamber and integral columns. The DRIE process involves the use of inductively coupled plasma etching and deposition in an alternating fashion, using fluorine based chemistry. Aspect ratios of 20:1 in etched structures are easily realized. The etch rate is typically 2 $\mu$m/min or higher.

After etching, the remaining photoresist is removed from the wafer, e.g., by oxygen plasma etching or wet chemical stripping in sulfuric acid. The substrate is then oxidized to cover the internal surfaces of the chamber, i.e., the chamber walls and surfaces of the columns, with an oxide layer. The oxide layer is preferably 1 to 100 nm thick, and may be formed using any well known technique, e.g., thermal growth, chemical or electrochemical growth, or deposition.

An electrically conductive material, e.g., aluminum, gold, or copper, is then deposited and patterned on the backside of the substrate to form the resistive heating element, temperature sensor, and bond pads. Different materials may be used to form the heating element and sensor. Specific techniques for patterning metal on a substrate are well known in the art. The substrate is then anodically bonded to a thin, e.g., 500 $\mu$m, pyrex™ glass cover. The glass cover has holes fabricated in it, e.g., by ultrasonic milling, which form the fluid ports to the chamber. After bonding, the substrate pair may be diced using a diamond saw. The resulting structure is shown schematically in FIG. 6.

The exact dimensions and structure of the microfluidic chip may be varied to suit the chip to a particular application. A specific example of one possible device according to the present invention is as follows. The device is 4.0 mm square and 0.9 mm thick. The extraction chamber has a depth of 200 $\mu$m and a length and width of 2.8 mm. The fluid ports each have a width of 0.4 mm. The device has a dense array of columns occupying an area 2.0 mm×2.8 mm within the chamber. The columns have a height of 200 $\mu$m, a cross sectional length of 50 $\mu$m, a cross sectional width of 7 $\mu$m, a gap distance of 8 $\mu$m between adjacent columns in a row, and a center to center spacing of 15 $\mu$m. There are roughly 7,000 columns in the array. Of course, these dimensions are exemplary of just one possible embodiment and are not intended to limit the scope of the invention. The specific dimensions of each material of the device may be varied in alternative embodiments, preferably within the general guidelines set forth earlier in this description.

The chip may be incorporated into a region of the cartridge with a flexible, polymeric coating, such as a silicone glue. Alternatively, a gasket may be fabricated with matching holes to the fluidic ports on the chip and a sealed fluidic assembly made between the microfluidic domain (the chip) and the macrofluidic domain (the cartridge body). The chip may be pressed tightly and sealed against the gasket material by bonding another plastic piece over the chip, thus completely encapsulating the chip within the cartridge.

Alternatively, the chip may be fused or welded to the cartridge directly without the use of a gasket. In a particularly advantageous embodiment, a portion of the cartridge itself may be the cover for the chip rather than using a separate substrate, e.g., the pyrex™ glass, to form the cover.

In this embodiment, the substrate 22 is inserted into the cartridge and sealed to a wall of the cartridge. The wall has holes in it forming the fluid ports to the extraction chamber.

One technique used to make integrated chip and plastic cartridges uses recessed regions in the plastic to accept the silicon/glass micromachined chip(s). The recessed regions are precisely dimensioned to accept and accurately locate the silicon/glass chip. This technique allows the small silicon/glass microfluidic chip(s) to be easily aligned to the macrofluidic channels, ports, and other fluidic regions molded into the plastic. The recess itself may contain a fluid port to connect with a fluid port on the bottom of the silicon/glass chip.

In addition, the use of recessed regions allows another plastic molded component to be easily laminated on top of the first silicon/glass/plastic assembly. This second technique is especially suitable for interfacing the molded fluid paths in the plastic to the small microfluidic openings (typically about 0.5 mm in diameter) which emerge onto the flat surfaces (on either side of the chip) of the silicon/glass chip. This technique can also provide a convenient means for accessing electrical contacts on the microfluidic chip, if necessary. In this case, a region in the laminated plastic is left open to allow easy access for wire bonding to the silicon/glass chip.

A third technique is the forming of molded plastic regions that are the inverse shape of anisotropically etched pyramidal pits in (100) silicon. This technique has several advantages. It allows for easy alignment between the silicon and the plastic and at the same time, minimizes the fluid dead volume where the plastic must be connected to an anisotropically etched fluid pit in a silicon chip.

A fourth technique is the use of laminated or patterned adhesive films to make fluid-tight seals between the various plastic and silicon/glass pieces. Materials such as polyimide or Mylar® can be formed in very thin sheets (on the order of 0.0254 mm) and coated on both sides with adhesive (curable by ultra violet or by temperature). The adhesive not only joins the two components, but also forms fluid-tight seals. Such sheets can be cut or punched into various shapes, thereby providing access holes or other shapes, then laminated onto the plastic and/or silicon/glass. For some applications, screen-printed adhesives may be more appropriate as fluid-tight seals.

Figure 15:
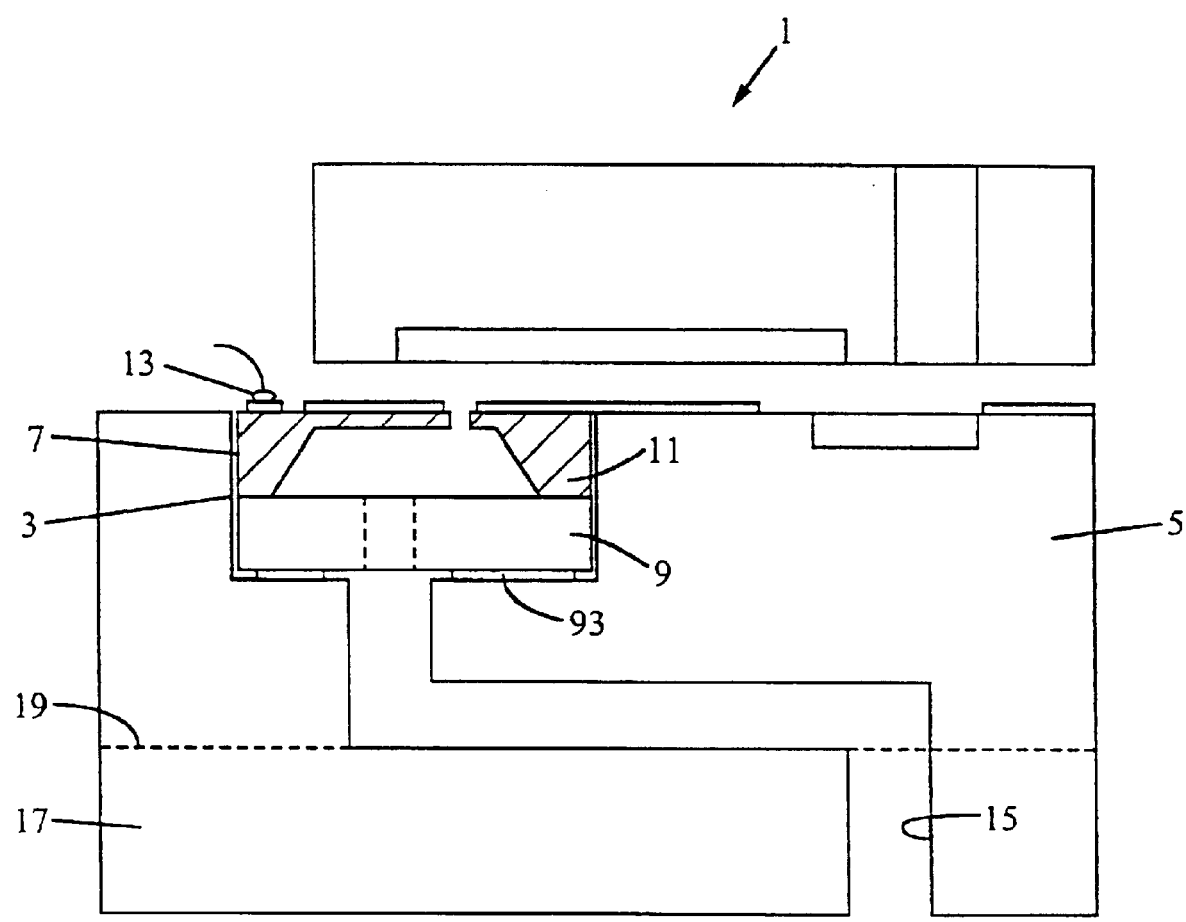
FIG. 15 is a partially exploded, cross-sectional view of a microfabricated chip embedded in a plastic cartridge.

FIG. 15 illustrates one type of integration between a silicon microfluidic chip 7 and a recess 3 within a cartridge 1. The precisely-dimensioned recess 3 is molded into the middle plastic portion 5 into which the chip 7 is inserted. The chip 7 has a glass portion 9 and silicon portion 11 and is accessible to wire connection 13. A channel 15 is molded into the middle plastic portion 5 and lower plastic portion 17. A laminated interface 19 aligns the channel of the middle and lower plastic components. A gasket or an adhesive 93 allows for fluid-tight lamination, sealing, and integration of the plastic portion and silicon-glass chip 7.

Figure 12:
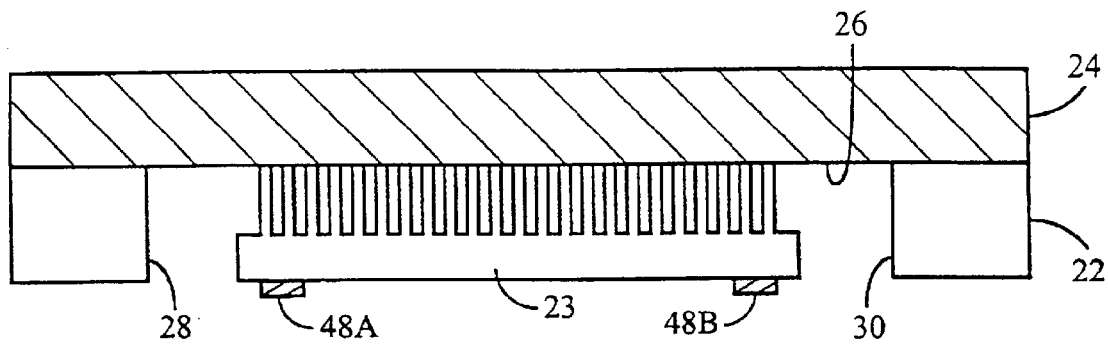
FIG. 12 is a schematic, cross sectional view of an alternative microfabricated chip for extracting analyte from a fluid sample.

FIG. 12 shows an alternative embodiment of the microfabricated chip in which the chip has fluid ports 28 and 30 formed in the base substrate 22 rather than the top substrate 24. The chip also includes electrodes 48A and 48B for heating the internal surfaces of the chamber 26. The electrodes are preferably positioned on opposite sides of the bottom wall 23 of the extraction chamber 26. The base substrate 22 is fabricated from a thermally conductive material, preferably silicon, so that the bottom wall 23 and integrally formed columns may be heated by applying an appropriate voltage across the electrodes 48A and 48B.

As in the previous embodiment, the chip may be used in combination with the cartridge, as previously described with reference to FIG. 2. The operation of the chip is analogous to the operation described above, except that the internal surfaces of the chamber 26 are heated by applying a voltage across the electrodes 48A and 48B. The bottom wall 23 functions as a resistive heating element for heating the chamber 26.

The microfluidic chip of FIG. 12 may be fabricated using a variety of techniques, including photolithography and/or micromachining. A preferred method for fabricating the chip will now be described.

A 100 mm, n-type (100), silicon wafer is used as starting material for the base substrate 22. The wafer preferably has a resistivity of 1 to 100 ohm-cm, depending on the desired final resistance between the electrodes 48A and 48B. The wafer thickness is preferably in the range of 350 to 600 $\mu$m, depending on the desired structure. Ohmic contacts are made by using phosphorous ion implantation into regions in the backside, preferably to a depth of 0.2 to 5 $\mu$m. Alternatively, a p-type silicon wafer may be used, and the ohmic contacts made using boron ion implantation. Implantation is followed by heating of the substrate to activate the dopant.

Next, the fluid ports 28 and 30 are formed by depositing and patterning a suitable masking material, e.g., silicon nitride, onto the backside of the wafer and anisotropic etching the silicon using the mask. The wafer is then patterned with photoresist on the frontside to obtain an etch mask for the DRIE process. As shown in FIG. 11, the etch mask defines a chamber pattern 44 for forming the extraction chamber in the substrate 22 and an array of column patterns 46 for forming a corresponding array of columns in the substrate. The patterned wafer is then etched using a DRIE process to form the extraction chamber and integral columns. The wafer is etched to a depth sufficient for the extraction chamber 26 to meet the fluid ports 28 and 30.

After etching, the remaining photoresist is removed from the wafer, and the substrate is then oxidized to cover the internal surfaces of the chamber 26 with an oxide layer, preferably 1 to 100 nm thick. An electrically conductive material, e.g., aluminum, gold, or copper, is then deposited and patterned over the doped regions on the backside of the substrate to form the electrodes 48A and 48B. The substrate 22 is then anodically bonded to a cover 24, preferably thin pyrex™ glass. After bonding, the substrate pair may be diced to form the final structure shown in FIG. 12.

Figure 13:
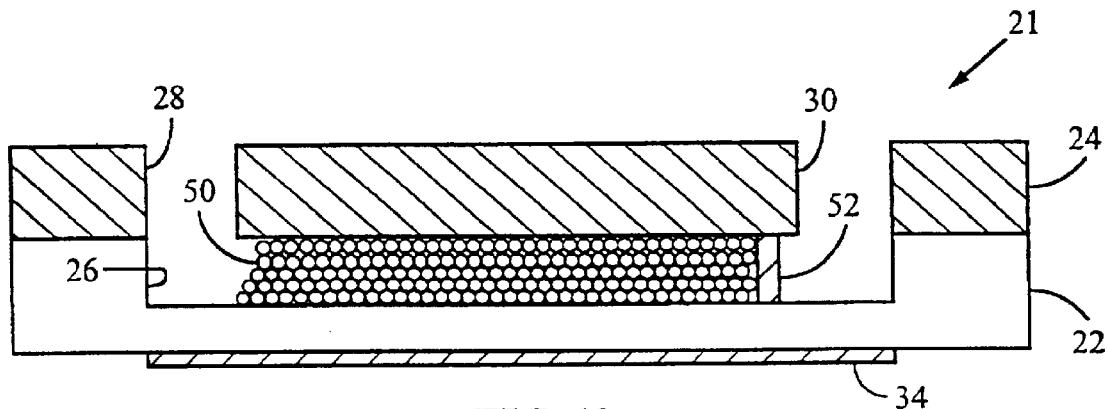
FIG. 13 is a schematic, cross sectional view of another microfabricated chip for extracting analyte from a fluid sample.

FIG. 13 shows a flow-through chip 21 according to another embodiment of the invention in which the internal attachment surfaces for capturing and eluting the analyte are formed by one or more solid supports contained within the chamber 26. As the fluid sample flows through the chamber 26, the analyte contacts and adheres to the solid support. To elute the analyte, the chamber 26 is heated while an elution fluid is forced to flow through the chamber, thus releasing the analyte from the solid support into the elution fluid. Suitable solid supports for capturing the analyte include filters, beads, fibers, membranes, glass wool, filter paper, gels, etc.

In the embodiment of FIG. 13, the solid support comprises glass beads 50 packed within the chamber 26. In embodiments that employ beads, fibers, wool, or gels as the solid support, the device preferably includes a barrier 52 disposed in the chamber 26 adjacent the outlet port 30 for preventing the solid support material from flowing out of the chamber. The barrier 52 may be any suitable retaining membrane or filter, such as a comb filter, for holding the solid support material within the chamber 26. Alternatively, the barrier 52 may comprise a plurality of internal structures, such as columns, formed within the chamber 26 and having a sufficiently small spacing to retain the solid support material.

The chip 21 may be used in combination with the cartridges of the invention to capture and elute target analyte, as previously described. The operation of the chip 21 is analogous to the operation described above, except that the analyte capture surfaces in the chamber 26 are provided by a solid support, such as the beads 50, rather than by an array of integrally formed microstructures.

The chip 21 may be fabricated using techniques similar to those described in earlier embodiments, including photolithography and micromachining. A preferred method for fabricating the chip will now be described. A 100 mm, n-type (100), 0.1 to 0.2 ohm-cm, silicon wafer is preferably used as starting material for the base substrate 22. The wafer is patterned with photoresist on the frontside to obtain an etch mask for a DRIE process. The etch mask defines a chamber pattern for forming the chamber 26 in the substrate 22 and a barrier pattern for forming internal barrier structures, preferably closely spaced columns, within the chamber 26. The patterned wafer is then etched using a DRIE process to form the chamber 26 and internal barrier structures. Of course, the structures should have a spacing smaller than the diameter of the beads 50 so that they will retain the beads in the chamber 26.

After etching, the remaining photoresist is removed from the wafer, and one or more electrically conductive materials is then deposited and patterned on the backside of the substrate to form a resistive heating element, temperature sensor, and bond pads. The substrate is then anodically bonded to a glass cover having holes that form the fluid ports 28 and 30. The beads 50 may be packed in the chamber 26 before or after attaching the cover, preferably after the cover is attached. The beads 50 are inserted through the inlet port 28. Of course, the barrier 52 should be in place before packing the beads 50 to prevent the beads from flowing out of the chamber 26.

Figure 14:
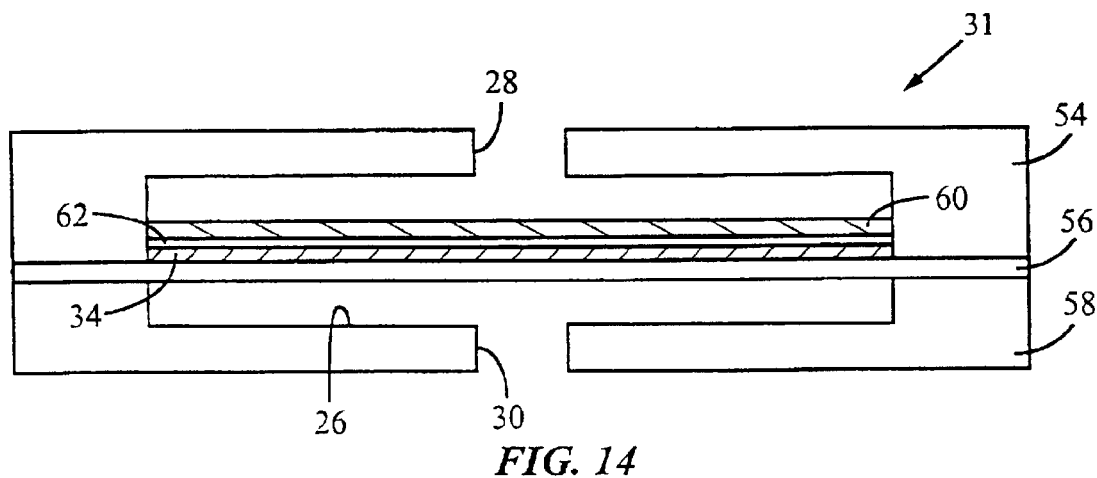
FIG. 14 is a schematic, cross sectional view of a microfabricated chip for extracting analyte from a fluid sample according to a further embodiment of the invention.

FIG. 14 shows a flow-through chip 31 according to another embodiment of the invention in which the solid support contained within the chamber 26 comprises a membrane or filter 60 for capturing the target analyte. The chip 31 includes a base substrate 58, a top substrate 54, and a middle substrate 56 sandwiched between the top and base substrates. The extraction chamber 26 is formed in the top and base substrates 54 and 58, and the filter 60 is preferably in thermal contact with the heater 34. Alternatively, the filter 60 may be disposed in the base substrate 58 adjacent the outlet port 30.

The resistive heating element 34 is preferably positioned on the middle substrate 56 for heating the chamber 26. The heating element 34 may be covered by a layer 62 of insulating material, e.g., silicon dioxide, silicon carbide, silicon nitride, plastic, glass, glue or other polymers, resist, or ceramic, for protecting the heating element 34 from fluids flowing through the chamber 26. The middle substrate 56 includes holes (not shown in the side view of FIG. 14) disposed around the heating element 34 to permit continuous fluid flow through the chamber from the inlet port 28 to the outlet port 30.

The heating element 34 may be a thin film of metal or polysilicon which is patterned on the substrate 56. Alternatively, the substrate 56 may be a thin plastic flex-circuit having the heating element 34. In another embodiment, the heating element 34 may comprise a laminated heater source, such as an etched foil-heating element, attached to the substrate 56. In embodiments where the heater is part of a laminated structure, the substrate 56 is the support for the heater. In yet another embodiment, the substrates 56 and 58, together with the heating element 34 and insulator layer 62, may all be fabricated from a single substrate using techniques known to those skilled in the art, e.g., thin film processing.

The chip 31 is used in combination with a cartridge of the present invention, as previously described. In operation, a fluid sample is forced to flow through the chip. As the fluid sample flows through the chamber 26, target analyte, e.g., nucleic acid, contacts and adheres to the filter 60. The chamber is optionally washed to remove unwanted particles. To elute the analyte, the chamber 26 is heated with the heating element 34 while an elution fluid is forced to flow through the chamber, releasing the analyte from the filter 60 into the elution fluid.

The top and base substrates 54 and 58 are preferably low cost molded plastic parts, and the middle substrate 56 is preferably a plastic flex circuit. The device 31 may be fabricated by precutting the filter 60 to size and then assembling the filter 60 and the substrates 54, 56, and 58 using adhesives, such as glue, or by welding, e.g. ultrasonic welding.

Figure 16:
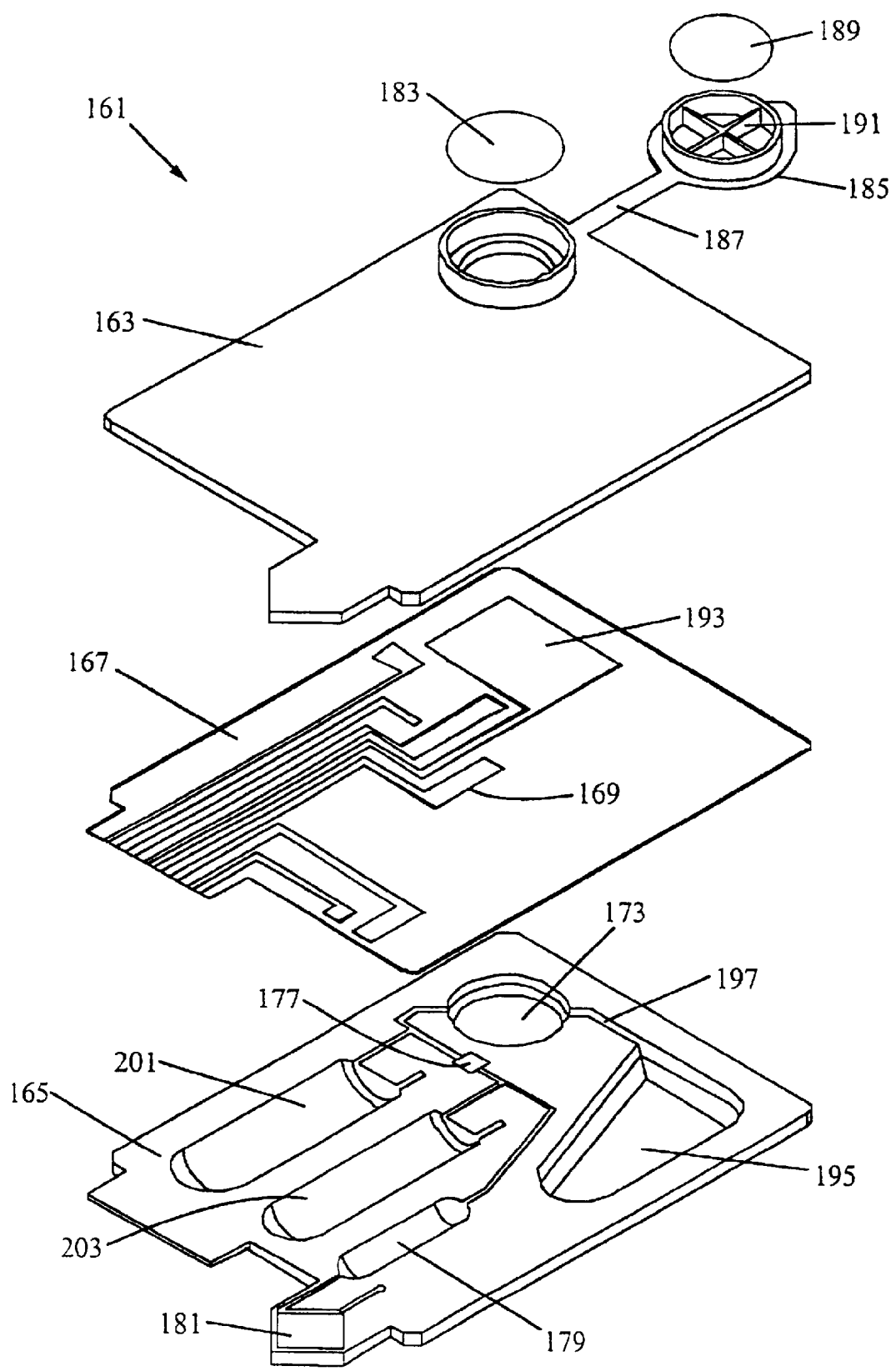
FIG. 16 is a partially exploded view of another cartridge showing a bottom plate, interactive regions, connecting channels, flex circuitry, fluid pouches, and a top plate with a fluid inlet port.

FIG. 16 shows another exemplary cartridge of the invention. The cartridge 161 is comprised of a top portion 163 and bottom portion 165 with a middle portion 167 therebetween. The middle portion 167 is preferably a printed circuit board (or flex circuit) having electrical circuitry 169. Mating of board 167 with bottom 165 forms one wall of the fluid flow regions. The sample flow path includes, in a downstream direction, a lysing chamber 173, a flow-through chip 177, and a vented waste chamber 203. The elution flow path includes the flow through chip 177, a reagent chamber 179, and a reaction chamber 181.

Figure 17:
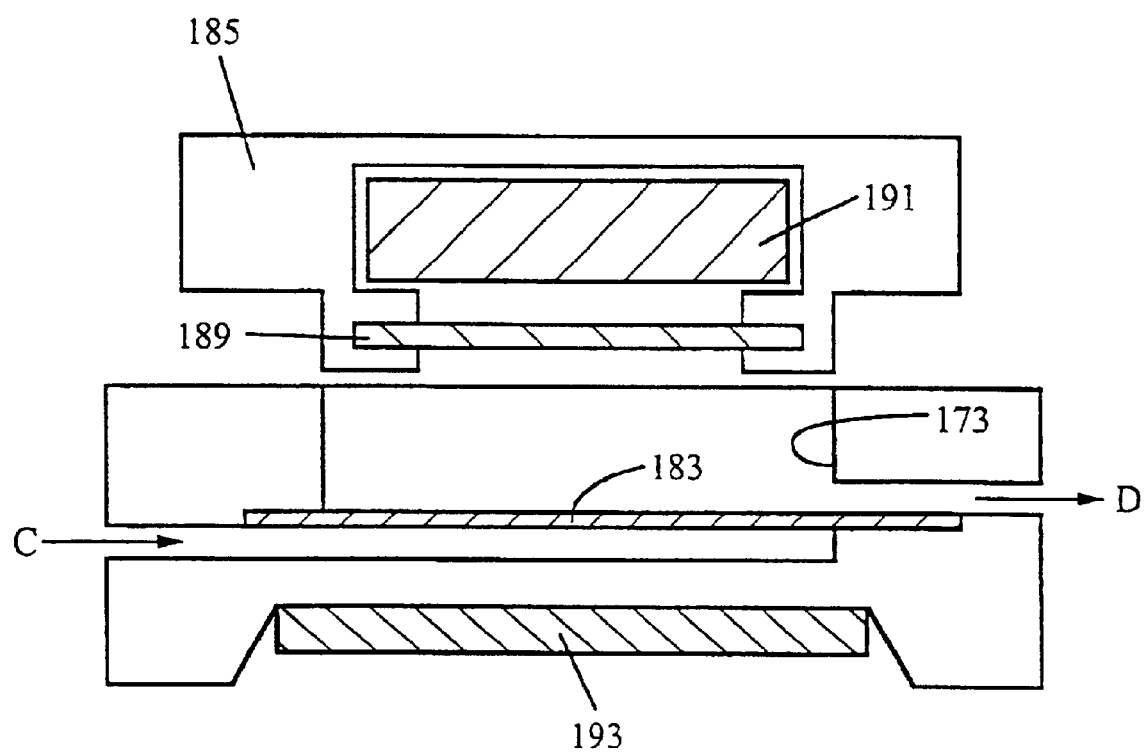
FIG. 17 is a cross-sectional view of a region of the cartridge of FIG. 16 containing filter paper for capturing analyte.

As shown in FIG. 16 and the detail of FIG. 17, the lysing chamber 173 has a chemically treated filter paper 183 which accepts the sample. A cap 185 is connected to the top by a flexible arm 187 and made to cover the lysing chamber 173 after the sample is added. The cap includes a membrane 189 made of material such as Goretex® which allows the transmission of gases but prevents the flow of liquid. A desiccant 191 is located in the cap on top of the membrane 189. A heater 193 is located on flex circuit 167 below the sample port and heats the filter paper 183 and the sample when the cap is in a closed position.

In operation, after the sample is added to the filter paper 183, the heater dries the sample and moisture rises through the membrane 189 and is absorbed into the desiccant 191. At the same time, chemicals impregnated in the paper lyse the cells and bind various biological molecules to the paper itself. The cartridge bottom includes a wash storage chamber 195 which is connected by channel 197 to the sample port in an area beneath the filter paper 183. Thus, after the sample is dried, wash fluid is forced to flow from C to D, as depicted in FIG. 17, through the filter paper 183 to wash out and/or elute processing chemicals which are present in the filter paper. The waste processing chemicals and wash are prevented from flowing into the desiccant by membrane 189 and exit the sample port through outlet D.

Figure 18:
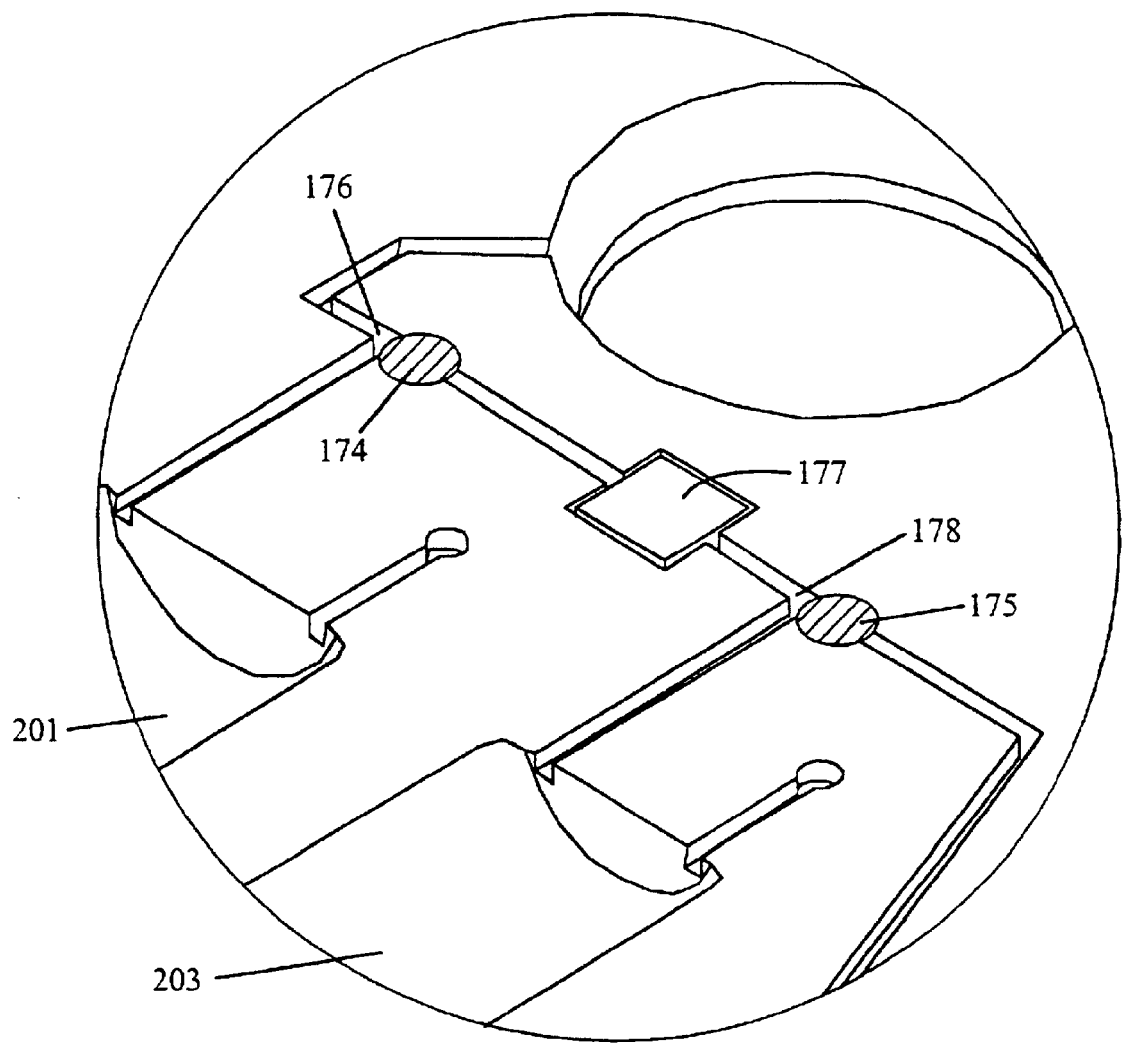
FIG. 18 is a schematic view of a flow diverter region of the cartridge of FIG. 16.

As shown in FIG. 16 and the detail of FIG. 18, waste fluid is washed away from the sample flow path and redirected into waste chamber 201 by a flow diverter 174. The flow diverters 174, 175 may comprise a capillary or hydrophobic membrane to allow fluid to pass when a threshold back pressure develops in the regions before the diverters. The waste fluid filling waste chamber 201 creates pressure in region 176. Once the waste chamber 201 is filled with fluid, the pressure in region 176 triggers the diverter 174 to allow fluid to pass. Simultaneously, the sample in lysing chamber 173 is heated by heater 193 causing the nucleic acid to be released from the filter paper 183 and flow out through outlet D.

The sample flows along the sample flow path through diverter 174 and into chip 177 where target analyte is extracted. Waste components flowing from the chip 177 are redirected by flow diverter 175 to flow into a second waste chamber 203. Waste components collecting in the second waste chamber 203 create back pressure in region 178. Once waste components fill the second waste chamber 203, the pressure in region 178 is sufficient to release diverter 175 and allow fluid to pass. Simultaneously, a voltage or heat is applied to the chip 177 through connectors in the flex circuit 167, releasing the target analyte. Thereby, the analyte flows down the elution flow path and into a reagent chamber 179 where predried reagents are reconstituted and mixed with the analyte. The mixture continues to flow into and fill the reaction chamber 181. The elution flow path ends at reaction chamber 181 where amplification, e.g. PCR, takes place.

Historically, the lysis step in sample processing has been a time consuming and difficult task, especially for spores and certain cell structures. In further embodiments, the present invention addresses this problem by providing a method and device for the rapid lysing of sample components, e.g., cells, spores, or microorganisms, using ultrasound. The ultrasonic lysing may be performed in a fully integrated cartridge, such as the cartridge of FIG. 2, or may be performed with a cartridge that performs only lysing of sample components.

Figure 19:
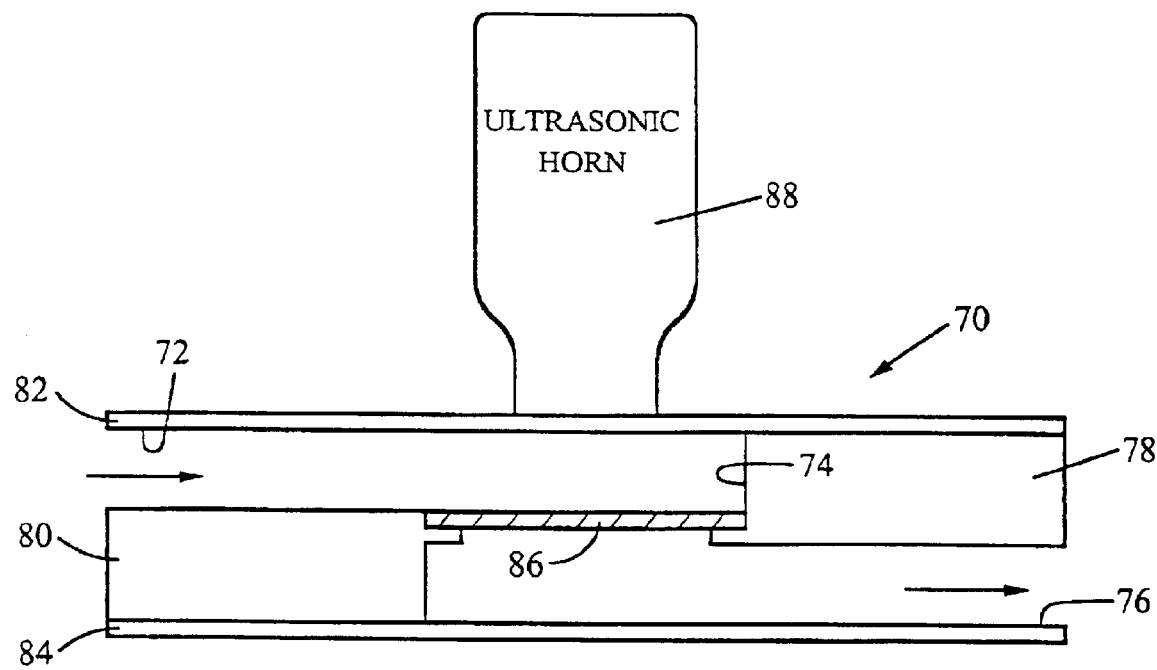
FIG. 19 is a schematic, side view of an ultrasonic horn coupled to a cartridge for lysing of sample components according to another embodiment of the invention.

FIG. 19 shows an exemplary device for lysing sample components, e.g., cells, spores, or microorganisms. The device includes a cartridge 70 having an inlet port 72 for introducing the sample into the cartridge, and a lysing chamber 74 in fluid communication with the inlet port 72 for receiving the sample. The cartridge also includes an outlet port 76 for exit of the sample from the chamber 74.

The chamber 74 contains a solid phase for capturing the components of the sample to be lysed. Suitable solid phases for capturing cells, spores, or microorganisms include, e.g., filters, beads, fibers, membranes, glass wool, filter paper, polymers and gels. The solid phase may capture the desired sample components through physical retention, e.g., size exclusion, through affinity retention, or through chemical selection. In the presently preferred embodiment, the solid phase comprises a membrane or filter 86 for capturing the components to be lysed. Suitable filter materials include glass, fiberglass, nylon, nylon derivatives, cellulose, cellulose derivatives, and other polymers. In an alternative embodiment, the solid phase comprises polystyrene, silica, agarose, cellulose, or acrylamide beads.

The device also includes an ultrasonic transducer, such as an ultrasonic horn 88, that is coupled to the cartridge for transferring ultrasonic energy to the components captured on the solid phase, e.g., captured on filter 86. A miniature ultrasonic horn is presently preferred as the transducer because it allows focusing of ultrasonic energy onto the components captured on the solid phase. To this end, it is also preferred that the horn 88 be coupled to the cartridge 70 such that the longitudinal axis of the horn 88 is perpendicular to the filter 86. Additionally, the horn 88 is preferably coupled directly to a wall of the chamber 74.

In operation, a sample fluid is introduced into the inlet port 72 and forced to flow into chamber 74. As the sample flows into the chamber 74, the sample components to be lysed are captured by the filter 86. The sample may be made to flow continually through the chamber 74, or the cartridge 70 may include flow controllers, e.g. valves, for holding the sample fluid in chamber 74 for lysis. Continuous flow processing is suitable for larger sample volumes, e.g. 1 mL or greater, while holding the sample in the chamber 74 may be appropriate for smaller sample volumes, e.g. 100 $\mu$l.

The sample components captured on the filter 86 are then lysed by transferring ultrasonic energy from the horn 88 to the captured components. The ultrasonic energy causes rapid lysis of cells, spores, or microorganisms captured on the filter. As a specific example, rapid lysis of spores in a 100 $\mu$l sample was accomplished by applying ultrasound for thirty seconds at a frequency of 47 kHz and an ultrasonic output of 50 watts. Ultrasonic output in the range of 10 to 60 watts is presently preferred. The ultrasonic lysis may be performed with or without the use of lysing reagents, e.g., chaotropes, detergents, salts, and reducing agents. The ultrasonic lysis permits the choice of buffer/resuspension solution related to the post lysis protocol (e.g., buffer that is non-inhibitory to PCR).

Typically, the ultrasonic transducer will be a separate component from the cartridge and coupled to the cartridge by an operator or machine. Alternatively, the transducer may be located in an external instrument that receives the cartridge for processing. In this embodiment, the transducer is preferably positioned in the instrument such that it presses against a wall of the lysing chamber when the cartridge is inserted into the instrument for processing. In another embodiment, the transducer may be built into the cartridge. In this embodiment, the cartridge includes suitable electrical connectors for connecting the transducer to a power supply. In embodiments in which the transducer is built into the cartridge, the transducer should be prevented from contacting the fluid sample directly, e.g., the transducer should be laminated or separated from the sample by a chamber wall.

The cartridge 70 may be fabricated using techniques previously described for the cartridge of FIG. 2. In particular, the cartridge 70 preferably comprises first and second molded plastic parts 78 and 80 which support filter 86. Filter 86 may optionally be heat sealed to the plastic parts 78 and 80. The cartridge also includes first and second plastic films 82 and 84 sealed to parts 78 and 80, respectively. Examples of suitable materials for the plastic parts 78 and 80 and for the films 82 and 84 include, e.g., polycarbonate, polystyrene, polypropylene, polyethylene, acrylic, and commercial polymers. To aid in the transfer of ultrasonic energy to the sample components, it is preferred that films 82 and 84 be relatively thin. Films 82 and 84 preferably have a thickness in the range of 0.01 to 0.5 mm, and more preferably have a thickness of about 0.05 mm.

Figure 20:
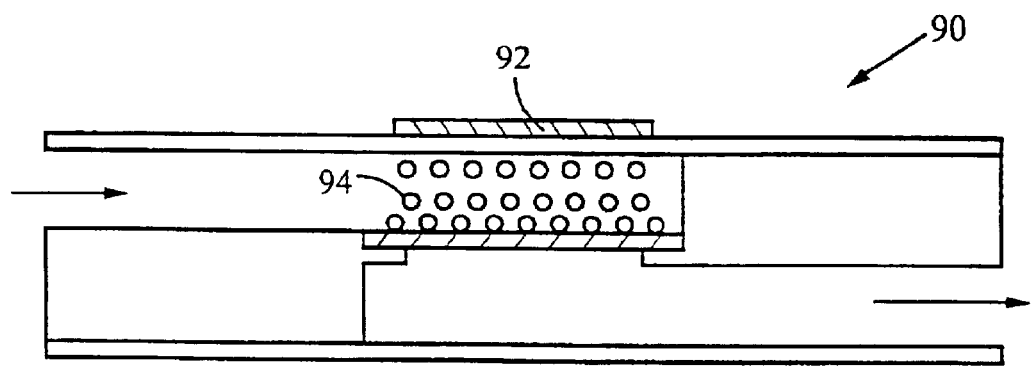
FIG. 20 is a schematic side view of an ultrasonic transducer coupled to a cartridge containing beads for lysing of sample components according to a further embodiment of the invention.

FIG. 20 shows another embodiment of a cartridge for ultrasonically lysing sample components. The cartridge 90 includes beads 94 in its lysing chamber for rupturing the components captured on the solid phase. The cartridge 90 also includes an ultrasonic transducer 92 in the form of a disk coupled to a wall of the chamber. In operation, the transducer 92 transfers ultrasonic energy to the captured sample components to effect lysing. The ultrasonic energy also agitates the beads so that the beads rupture the sample components to effect lysing. Suitable beads for rupturing sample components include polystyrene and silica. The beads may be porous or non-porous and preferably have a diameter in the range of 1 to 200 $\mu$m. As a specific example, the ultrasonic lysis chamber may have a volume capacity of 110 μL and contain 10 μL of glass beads.

Although the embodiments of FIGS. 19 and 20 show cartridges that perform only lysing functions, it is to be understood that the ultrasonic lysis of the present invention may be incorporated into cartridges that perform a variety of other function. For example, referring again to FIG. 2, an ultrasonic transducer may be coupled to the lysing chamber 119 to lyse cells, spores, or microorganisms in a fluid sample. Further, beads could also be put in the chamber 119 to rupture the sample components. In another embodiment, a heating element may be used in place of or in combination with an ultrasonic transducer to lyse sample components captured on a solid phase.

Although the above description contains many specificities, these should not be construed as limitations on the scope of the invention, but merely as illustrations of some of the presently preferred embodiments. Many possible variations and modifications to the invention will be apparent to one skilled in the art upon consideration of this disclosure. Therefore, the scope of the invention should be determined by the following claims and their legal equivalents.

What is claimed is:

1. A device for use with an ultrasonic transducer to lyse components of a fluid sample, the device comprising:
   a) a cartridge having:
      i) a lysing chamber;
      ii) an inlet port in fluid communication with the lysing chamber; and
      iii) an outlet port for exit of the sample from the lysing chamber, wherein the inlet and outlet ports are positioned to permit flow of the sample through the lysing chamber, and wherein the chamber is defined by at least one wall having an external surface to which the ultrasonic transducer may be coupled;
   b) at least one membrane or filter positioned in the lysing chamber for capturing the sample components to be lysed as the sample flows through the chamber; and
   c) beads disposed in the lysing chamber for rupturing the sample components.

2. The device of claim 1, wherein the wall comprises a plastic film having a thickness in the range of 0.01 to 0.5 mm.

3. A device for use with an ultrasonic transducer to lyse components of a fluid sample, the device comprising:
   a) a cartridge having:
      i) a lysing chamber;
      ii) an inlet port in fluid communication with the lysing chamber; and
      iii) an outlet port for exit of the sample from the lysing chamber, wherein the inlet and outlet ports are positioned to permit flow of the sample through the lysing chamber; and
   b) at least one solid phase in the lysing chamber for capturing the sample components to be lysed as the sample flows through the chamber;
   wherein the lysing chamber is defined by at least one wall having an external surface to which the ultrasonic transducer may be coupled, and wherein the wall comprises a plastic film having a thickness in the range of 0.01 to 0.5 mm.

4. The device of claim 1, wherein the solid phase comprises a membrane or filter for capturing the sample components, and the device further comprises beads in the lysing chamber for rupturing the sample components.

* * * * *